United States Patent
Bru Roig et al.

(10) Patent No.: US 11,993,760 B2
(45) Date of Patent: May 28, 2024

(54) 2-FURYL- AND 2-THIENYL-SUBSTITUTED DI- AND TETRAHYDROPYRANS FOR USE AS AROMA CHEMICALS

(71) Applicant: BASF SE, Ludwigshafen am Rhein (DE)

(72) Inventors: Miriam Bru Roig, Ludwigshafen am Rhein (DE); Manuel Danz, Ludwigshafen am Rhein (DE); Ralf Pelzer, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 788 days.

(21) Appl. No.: 17/059,017

(22) PCT Filed: May 24, 2019

(86) PCT No.: PCT/EP2019/063516
§ 371 (c)(1),
(2) Date: Nov. 25, 2020

(87) PCT Pub. No.: WO2019/224373
PCT Pub. Date: Nov. 28, 2019

(65) Prior Publication Data
US 2021/0207057 A1    Jul. 8, 2021

(30) Foreign Application Priority Data
May 25, 2018   (EP) ..................... 18174317

(51) Int. Cl.
| | | |
|---|---|---|
| *C07D 407/04* | (2006.01) | |
| *C07D 409/04* | (2006.01) | |
| *C11B 9/00* | (2006.01) | |

(52) U.S. Cl.
CPC ........... *C11B 9/008* (2013.01); *C07D 407/04* (2013.01); *C07D 409/04* (2013.01)

(58) Field of Classification Search
USPC .......................................................... 512/11
See application file for complete search history.

(56) References Cited

U.S. PATENT DOCUMENTS

| | | |
|---|---|---|
| 4,914,083 A | 4/1990 | Wiegers et al. |
| 4,962,090 A | 10/1990 | Sprecker et al. |
| 5,219,836 A | 6/1993 | Watkins et al. |
| 2020/0325112 A1 | 10/2020 | Hickmann et al. |

FOREIGN PATENT DOCUMENTS

| | | | |
|---|---|---|---|
| EP | 0383446 A2 | 8/1990 | |
| EP | 1927593 A1 | 6/2008 | |
| EP | 2112144 A1 | 10/2009 | |
| WO | 2017/207539 A1 | 12/2017 | |
| WO | WO-2017207539 A1 * | 12/2017 | ........... C07D 309/10 |

OTHER PUBLICATIONS

Liu Lupi Ng et al: "A General Catalytic Asymmetric Prins Cyclization", Journal of the American Chemical Society, American Chemical Society, United States, vol. 138, No. 34, Aug. 31, 2016, pp. 10822-10825, XP002785092.

Marco J A et al: "Synthesis of conjugated @c- and @d-lactones from aldehydes and ketones via a vinylation(allylation)-ring closing metathesis-oxidation sequence", Tetrahe, Elsevier Science Publishers, Amsterdam, NL, vol. 59, No. 23, Jun. 2, 2003, pp. 4085-4101, XP004427967.

International Preliminary Report on Patentability received for PCT Patent Application No. PCT/EP2019/063516, dated Dec. 10, 2020, 9 pages.

International Search Report and Written Opinion received for PCT Patent Application No. PCT/EP2019/063516, dated Jul. 2, 2019, 11 pages.

* cited by examiner

*Primary Examiner* — Jessica Whiteley
(74) *Attorney, Agent, or Firm* — Faegre Drinker Biddle & Reath LLP

(57) ABSTRACT

The present invention relates to the use of 2-furyl- and 2-thienyl-substituted di- and tetrahydropyrans of the formula (I) wherein the variables are as defined in the claims and the description, as aroma chemicals; to aroma chemical compositions comprising at least one 2-furyl- or 2-thienyl-substituted di- or tetrahydropyran and to a method for preparing an aroma chemical composition. The present invention further relates to specific 2-furyl- and 2-thienyl-substituted di- and tetrahydropyrans and to a method for their preparation.

25 Claims, No Drawings

2-FURYL- AND 2-THIENYL-SUBSTITUTED DI- AND TETRAHYDROPYRANS FOR USE AS AROMA CHEMICALS

CROSS-REFERENCE TO RELATED APPLICATIONS

This application is a national stage application (under 35 U.S.C. § 371) of PCT/EP2019/063516, filed May 24, 2019, which claims benefit of European Application No. 18174317.0, filed May 25, 2018, both of which are incorporated herein by reference in their entirety.

The present invention relates to the use of 2-furyl- and 2-thienyl-substituted di- and tetrahydropyrans as aroma chemicals, to aroma chemical compositions comprising at least one 2-furyl- or 2-thienyl-substituted di- or tetrahydropyran and to a method for preparing an aroma chemical composition, in particular a fragranced composition, specifically a fragranced ready-to-use composition, which comprises incorporating at least one 2-furyl- or 2-thienyl-substituted di- or tetrahydropyran into such a composition. The present invention further relates to specific 2-furyl- and 2-thienyl-substituted di- and tetrahydropyrans and to a method for their preparation.

BACKGROUND OF THE INVENTION

Aroma chemicals, especially fragrances, are of great interest especially in the field of cosmetics and cleaning and laundry compositions. Fragrances of natural origin are mostly expensive, often limited in their available amount and, on account of fluctuations in environmental conditions, are also subject to variations in their content, purity etc. To circumvent these undesirable factors, it is therefore of great interest to create synthetic substances which have organoleptic properties that resemble more expensive natural fragrances or which have novel and interesting organoleptic profiles.

Despite a large number of already existing synthetic aroma chemicals (fragrances and flavorings), there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should, however, also have additional positive secondary properties, such as e.g. an efficient preparation method, the possibility of providing better sensory profiles as a result of synergistic effects with other fragrances, a higher stability under certain application conditions, a higher extendability, a better staying power, etc.

However, since even small changes in chemical structure bring about massive changes in the sensory properties such as odor and also taste, the targeted search for substances with certain sensory properties such as a certain odor is extremely difficult. The search for new fragrances and flavorings is therefore in most cases difficult and laborious without knowing whether a substance with the desired odor and/or taste will even actually be found.

2,4,4-Trisubstituted tetrahydropyran compounds have been repeatedly mentioned as aroma chemicals. For example, EP 0383446 A2 describes 2,4,4-trisubstituted tetrahydropyran of the formula (A), wherein $R^I$ is methyl or ethyl and $R^{II}$ is linear or branched $C_2$-$C_4$-alkyl or $C_2$-$C_4$-alkenyl.

U.S. Pat. No. 4,962,090 describes 2,4-disubstituted and 2,2,4-trisubstituted tetrahydropyranyl-4-ethers of the formula (B), wherein R' represents methyl or ethyl and $R^a$ and $R^b$ are selected from hydrogen, phenyl, $C_1$-$C_8$-alkyl and $C_2$-$C_8$-alkenyl or taken together represent $C_5$-$C_{12}$-cycloalkyl or alkylcycloalkyl.

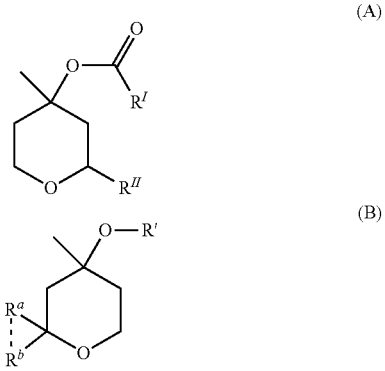

L. Liu et al., J. Am. Chem. Soc. 2016, 138, 10822-10825 describe a method for preparing chiral 2-substituted 4-methylene tetrahydropyrans by asymmetric Prins cyclization of an aromatic or aliphatic aldehyde with 3-methylprop-3-en-1-ol. Inter alia, the synthesis of 2-(furan-2-yl)-4-methylenetetrahydropyran and its regioisomer is described.

J. A. Marco et al. describe in Tetrahedron 2003, 59, 4085-4101 the synthesis of conjugated γ- and δ-lactones from aldehydes and ketones via ring-closing metathesis. Inter alia the synthesis of 2-(2-furyl)-4-methyl-3,6-dihydro-2H-pyran is described.

So far, 2-furyl- and 2-thienyl-substituted di- and tetrahydropyrans have not yet been suggested as aroma chemicals.

SUMMARY OF THE INVENTION

It was an object of the present invention to provide substances exhibiting pleasant organoleptical properties and which can be advantageously used as aroma chemicals. It was a further object of the present invention to provide substances which can be used as an aroma chemical in ready-to-use compositions. In particular, odor-intensive substances having a pleasant odor are sought. Furthermore, these aroma chemicals should be combinable with other aroma chemicals, allowing the creation of novel advantageous sensory profiles. In addition, these aroma chemicals should be obtainable from readily available starting materials, allowing their fast and economic manufacturing.

It was surprisingly found that these and further objects are achieved by the compounds of the formula (I), by mixtures thereof [meaning mixtures of two or more different compounds (I), e.g. 2, 3 or 4 different compounds (I)], by stereoisomers thereof and by mixtures of stereoisomers thereof.

Accordingly, a first aspect of the present invention relates to the use of a compound of the general formula (I), including the stereoisomers thereof, as an aroma chemical:

(I)

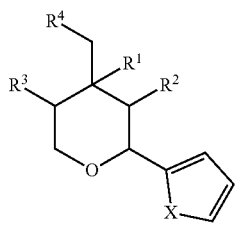

wherein
X is O or S;
R$^1$ is hydrogen, OH, O—C$_1$-C$_4$-alkyl or O—(C=O)—R$^5$;
R$^2$, R$^3$, R$^4$ are hydrogen;
or one of R$^2$, R$^3$, R$^4$ together with R$^1$ represents a double bond; and
R$^5$ is selected from the group consisting of hydrogen and C$_1$-C$_4$-alkyl.

The invention also relates to the use of a mixture of different compounds of the formula (I), including mixtures of double bond isomers, and of mixtures of stereoisomers thereof, as aroma chemicals.

The present invention further relates to aroma chemical compositions comprising at least one compound of formula (I), a stereoisomer thereof or a mixture of stereoisomers thereof, as defined above, and at least one further compound selected from the group consisting of aroma chemicals different from compounds (I) and non-aroma chemical carriers.

It was further found that the compounds of the general formula (I) generally exhibit a pleasant and characteristic odor and can be used to produce fragranced ready-to-use compositions. In addition, they can advantageously be combined with other aroma chemicals different from compounds (I) to create new scent profiles.

Therefore, the present invention further relates to a method of preparing an aroma chemical composition, in particular a fragranced composition, specifically a fragranced ready-to-use composition, comprising incorporating at least one compound of formula (I), a stereoisomer thereof or a mixture of stereoisomers thereof, into a composition, in particular into a ready-to-use composition.

The invention also relates to the use of a compound of formula (I), a stereoisomer thereof, a mixture of stereoisomers thereof or a mixture of different compounds (I), as defined above, for modifying the scent character of a fragranced ready-to-use composition.

Amongst the group of compounds of formula (I), the 2-(2-furyl)-tetrahydropyran compounds of formula (I.a) described hereinafter and the 2-(2-thienyl)-tetrahydropyran compounds of formula (I.b) described hereinafter have not been described in the art.

Therefore, the present invention also relates to novel compounds of the general formula (I.a)

(I.a)

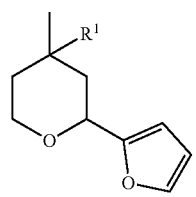

wherein
R$^1$ is hydrogen, OH, O—C$_1$-C$_4$-alkyl or O—(C=O)—R$^5$, and
R$^5$ is selected from the group consisting of hydrogen and C$_1$-C$_4$-alkyl;
a mixture of different compounds (I.a), a stereoisomer thereof or a mixture of stereoisomers thereof;
and to a method for producing such compounds.

Furthermore, the present invention relates to novel compounds of the general formula (I.b)

(I.b)

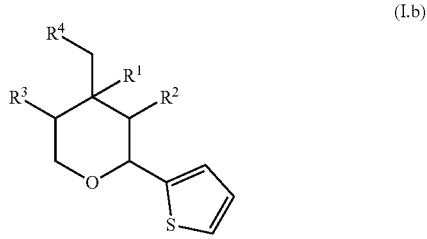

wherein
R$^1$ is hydrogen, OH, O—C$_1$-C$_4$-alkyl or O—(C=O)—R$^5$,
R$^2$, R$^3$, R$^4$ are hydrogen;
or one of R$^2$, R$^3$, R$^4$ together with R$^1$ represents a double bond;
R$^5$ is selected from the group consisting of hydrogen and C$_1$-C$_4$-alkyl;
a mixture of different compounds (I.b), a stereoisomer thereof or a mixture of stereoisomers thereof;
and to a method for producing such compounds.

The invention also relates to a mixture of at least two different compounds of the formula (I). In particular, the mixture comprises two or three double bond isomers of the compound of the formula (I).

The compounds of formula (I), their mixtures, their stereoisomers or the mixtures of their stereoisomers possess advantageous organoleptic properties, in particular a pleasant odor. Therefore, they can be favorably used as an aroma chemical for example in perfume compositions, body care compositions (including cosmetic compositions, products for oral and dental hygiene, hygiene articles, cleaning compositions (including dishwashing compositions), textile detergent compositions, compositions for scent dispensers, foods, food supplements, pharmaceutical compositions, crop protection compositions and other ready-to-use compositions.

By virtue of their physical properties, the compounds of formula (I), their stereoisomers or the mixtures of their stereoisomers have particularly good, virtually universal solvent properties for other fragrances and other customary ingredients in fragranced ready-to-use compositions such as, in particular, perfume compositions. Therefore, the compounds of formula (I), their stereoisomers or the mixtures of their stereoisomers are favorably combinable with other aroma chemicals, allowing, in particular, the creation of perfume compositions having novel advantageous sensory profiles.

Furthermore, the compounds of formula (I), their stereoisomers or the mixtures of their stereoisomers can be produced in good yields and purities by a one-step or a two-step synthesis, respectively, starting from readily available starting compounds. Thus, the compounds of formula (I), their stereoisomers or the mixtures of their stereoisomers, can be produced in large scales and in a simple and cost-efficient manner.

DETAILED DESCRIPTION OF THE INVENTION

In the context of the present invention, the expression "$C_1$-$C_4$-alkyl" refers to methyl, ethyl, n-propyl, isopropyl, n-butyl, sec-butyl, isobutyl and tert-butyl. Preferably, the expression "$C_1$-$C_4$-alkyl" refers to $C_1$-$C_3$-alkyl, i.e. to methyl, ethyl, n-propyl and isopropyl, and in particular to $C_1$-$C_2$-alkyl, i.e. to methyl and ethyl.

If one of $R^2$, $R^3$, $R^4$ together with $R^1$ represents a double bond, this means of course that the double bond is formed by the bond present between the carbon atoms to which $R^2$, $R^3$ or $R^4$ and $R^1$ are bound and a bond formed by $R^2$, $R^3$ or $R^4$ together with $R^1$. Thus, if $R^2$ together with $R^1$ represents a double bond, this results in a compound of formula (I-1). If $R^3$ together with $R^1$ represents a double bond, this results in a compound of formula (I-2). If $R^4$ together with $R^1$ represents a double bond, this results in a compound of formula (I-3).

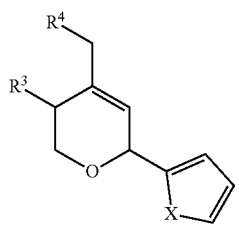

(I-1)

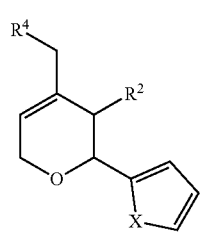

(I-2)

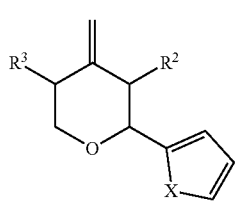

(I-3)

These compounds can be regarded as double bond isomers of each other.

Seeing that $R^3$ and $R^4$ in compounds I-1 are H, $R^2$ and $R^4$ in compounds I-2 are H, and $R^2$ and $R^3$ in compounds I-3 are H, compounds of formulae I-1, I-2 and I-3 can be depicted more simply as follows:

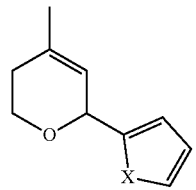

(I-1)

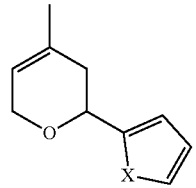

(I-2)

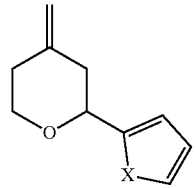

(I-3)

If $R^1$ is H, the compound (I) is a compound of formula (I-4). If $R^1$ is OH, the compound (I) is a compound of formula (I-5). If $R^1$ is O—$C_1$-$C_4$-alkyl, the compound (I) is a compound of formula (I-6). If $R^1$ is O—(C=O)—$R^5$, the compound (I) is a compound of formula (I-7).

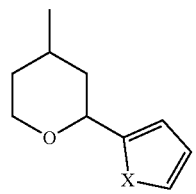

(I-4)

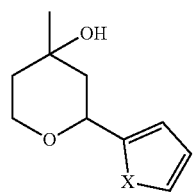

(I-5)

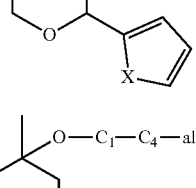

(I-6)

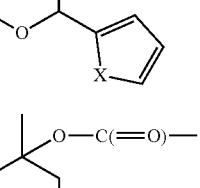

(I-7)

The term "stereoisomers" encompasses both optical isomers, such as enantiomers or diastereomers, the latter existing due to more than one stereogenic center in the molecule, as well as geometrical isomers (cis/trans isomers) as a specific form of diastereomers. The compounds of the formula (I) have at least one stereogenic center, namely the carbon atom of the di- or tetrahydropyran ring carrying the furan (X=O) or thiophene ring (X=S). In case that $R^1$ is hydrogen, OH, O—$C_1$-$C_4$-alkyl or O—(C=O)—$R^5$, the compound of formula (I) has one more stereogenic center (namely at the carbon atom of the di- or tetrahydropyran carrying $R^1$). The invention provides both the pure enantiomers or diastereomers and their mixtures and the use according to the invention of pure enantiomers or of pure diastereomers of the compound (I) or of mixtures thereof.

In the present context, the term "compound I", "compound (I)" or "compound of formula (I)", when not defined as a specific stereoisomer or a specific mixture of stereoisomers, refers to the form of the compound as it is obtained in a non-stereoselective method used for its production. The term is however also used if it is not necessary or not possible to specify in more detail the stereochemistry of the compound (I).

If in the following the compound of formula (I) is defined to be a specific, defined compound (and not to be a mixture of different compounds I), this means that the compound contains less than 5% by weight, preferably less than 3% by weight and in particular preferably less than 1% by weight of other compounds I, relative to the overall weight of the specific, defined compound I and the optionally present other compound(s) I.

In mixtures containing different compounds (I), these may differ in the definition of one or more radicals $R^1$ to $R^4$ and/or X. Preferably, the compounds in the mixture differ only in the definition of one or more radicals $R^1$ to $R^4$. More preferably, the mixture contains two or three of the compounds (I-1), (I-2) and (I-3). Due to the preparation process, such mixtures may moreover contain minor amounts of compound (I-5). "Minor amount" means less than 3% by weight, preferably less than 1% by weight, relative to the total weight of the compounds (I-1), (I-2), (I-3) and (I-5) contained in the mixture. In general, the mixture of two or three of the compounds (I-1), (I-2) and (I-3) is a mixture of double bond isomers, which means that in all compounds (I-1), (I-2) and (I-3) contained in the mixture (and in compound (I-5), if present) X has the same meaning and is thus either in each case O or is in each case S. Mixtures in which X in (I-1), (I-2) and/or (I-3) has different meanings are also suitable for the object of the present invention, but are less economic, seeing that mixtures in which X in all compounds (I) has the same meaning are often formed automatically in the production process.

In a preferred embodiment of the present invention, in compounds of the general formula (I), X is O.

In another preferred embodiment of the present invention, in compounds of the general formula (I), X is S.

In a preferred embodiment of the present invention, in compounds of the general formula (I), one of $R^2$, $R^3$, $R^4$ together with $R^1$ represents a double bond.

More preferably, the compound of formula (I) is a compound (I-1), where $R^2$ together with $R^1$ represents a double bond, or is a compound (I-2), where $R^3$ together with $R^1$ represents a double bond, or is a compound (I-3), where $R^4$ together with $R^1$ represents a double bond, or is a mixture of at least two of the compounds (I-1), (I-2) and (I-3). Such mixtures of at least two of the compounds (I-1), (I-2) and (I-3) are preferably mixtures of double bond isomers of compounds (I), meaning that in all compounds (I-1), (I-2), (I-3) contained in the mixture, X has the same meaning.

The compound (I-1), the compound (I-2), the compound (I-3) or the mixture of at least two compounds (I-1), (I-2) and (I-3) may contain a minor amount of a compound I in which $R^1$ is OH [compound (I-5)]. "Minor amount" means less than 3% by weight, preferably less than 1% by weight, relative to the total weight of the compounds (I-1), (I-2) and (I-3) or a mixture thereof, including the compound I in which $R^1$ is OH.

In a particular embodiment, the compound of formula (I) is a compound (I-1), where $R^2$ together with $R^1$ represents a double bond. In another particular embodiment, the compound of formula (I) is a compound (I-2), where $R^3$ together with $R^1$ represents a double bond. In another particular embodiment, the compound of formula (I) is a compound (I-3), where $R^4$ together with $R^1$ represents a double bond. Specifically, the compound of formula (I) is a compound (I-2).

In yet another particular embodiment, the compound of formula (I) is a mixture of at least two of the compounds (I-1), (I-2) and (I-3). More particularly, the mixture contains compound I-2 and one or both of compounds I-1 and I-3. In an alternative more particular embodiment, the mixture contains compounds I-1 and I-2 and optionally also compound I-3. In yet another alternative more particular embodiment, the mixture contains compounds (I-2) and (I-3); or contains all three compounds (I-1), (I-2) and (I-3).

In particular, the mixture contains compounds I-2 and I-3 and optionally also compound I-1, where compound I-1 is contained in an amount of from 0 to 10% by weight, compound I-2 is contained in an amount of from 1 to 80% by weight, and compound I-3 is contained in an amount of from 15 to 99% by weight, relative to the total weight of compounds I-1, I-2 and I-3. Preferably, the mixture is a mixture of double bond isomers, meaning that in compounds (I-2) and (I-3) contained in the mixture, X has the same meaning. Specifically, the mixture contains all three compounds (I-1), (I-2) and (I-3), where compound I-1 is contained in an amount of from 0.1 to 10% by weight, compound I-2 is contained in an amount of from 1 to 79.9% by weight, and compound I-3 is contained in an amount of from 15 to 99% by weight, relative to the total weight of compounds I-1, I-2 and I-3. Preferably, the mixture is a mixture of double bond isomers, meaning that in all compounds (I-1), (I-2), (I-3) contained in the mixture, X has the same meaning.

In a specific embodiment of the binary mixture of compounds (I-2) and (I-3), compound (I-3) predominates, i.e. it is present in an amount of more than 50% by weight, based on the weight of the mixture consisting of compounds (I-2) and (I-3). In particular, it is present in an amount of from 70 to 99% by weight, more particularly from 75 to 98% by weight and specifically from 75 to 95% by weight, based on the weight of the mixture consisting of compounds (I-2) and (I-3); the difference to 100% being the compound (I-2).

In a specific embodiment of the ternary mixture of compounds (I-1), (I-2) and (I-3), compound (I-2) predominates. In particular, it is present in an amount of from 50 to 80% by weight, more particularly from 55 to 75% by weight and specifically from 60 to 70% by weight, based on the weight of the mixture consisting of compounds (I-1), (I-2) and (I-3). Specifically, in the ternary mixture the compound (I-3) is the second most frequent component, and is in particular present in an amount of from 15 to 45% by weight, more particularly from 20 to 40% by weight and specifically from 28 to 39.5% by weight, based on the weight of the mixture consisting of compounds (I-1), (I-2) and (I-3). The compound (I-1) is specifically the minor compound and is in particular present in an amount of from 0.1 to 10% by weight, more particularly from 0.5 to 5% by weight and specifically from 0.5 to 2% by weight, based on the weight of the mixture consisting of compounds (I-1), (I-2) and (I-3). As a matter of course, the percentages of compounds (I-1), (I-2) and (I-3) add to 100%.

In another specific embodiment of the ternary mixture of compounds (I-1), (I-2) and (I-3), compound (I-3) predominates. In particular, it is present in an amount of from 50 to 90% by weight, more particularly from 55 to 90% by weight and specifically from 55 to 85% by weight, based on the weight of the mixture consisting of compounds (I-1), (I-2) and (I-3). Specifically, in the ternary mixture the compound (I-2) is the second most frequent component, and is in particular present in an amount of from 9 to 45% by weight, more particularly from 9 to 44.5% by weight and specifically from 13 to 44.5% by weight, based on the weight of the mixture consisting of compounds (I-1), (I-2) and (I-3). The compound (I-1) is specifically the minor compound and is in particular present in an amount of from 0.1 to 10% by weight, more particularly from 0.5 to 5% by weight and specifically from 0.5 to 2% by weight, based on the weight of the mixture consisting of compounds (I-1), (I-2) and (I-3). As a matter of course, the percentages of compounds (I-1), (I-2) and (I-3) add to 100%.

Specifically, the mixture contains compounds I-1, I-2 and I-3, where compound I-1 is contained in an amount of from 0.5 to 1.5% by weight, compound I-2 is contained in an amount of from 15 to 73.5% by weight, and compound I-3 is contained in an amount of from 25 to 84.5% by weight, relative to the total weight of compounds I-1, I-2 and I-3. As a matter of course, the percentages of compounds (I-1), (I-2) and (I-3) add to 100%.

As said, in such mixtures of at least two of the compounds (I-1), (I-2) and (I-3), in all compounds (I-1), (I-2), (I-3) contained in the mixture, X preferably has the same meaning.

In another preferred embodiment of the present invention, in compounds of the general formula (I), $R^1$ is hydrogen [the compound (I) being thus a compound (I-4)].

In another preferred embodiment of the present invention, in compounds of the general formula (I), $R^1$ is OH [the compound (I) being thus a compound (I-5)].

In another preferred embodiment of the present invention, in compounds of the general formula (I), $R^1$ is O—$C_1$-$C_4$-alkyl [the compound (I) being thus a compound (I-6)]. In particular $R^1$ is O—$C_1$-$C_2$-alkyl (i.e. $R^1$ is methoxy or ethoxy). Specifically, $R^1$ is methoxy.

In another preferred embodiment of the present invention, in compounds of the general formula (I), $R^1$ is O—(C=O)—$R^5$ [the compound (I) being thus a compound (I-7)]. Preferably, $R^5$ is $C_1$-$C_4$-alkyl, in particular $C_1$-$C_2$-alkyl. Specifically, $R^5$ is methyl (i.e. $R^1$ is acetoxy).

More preferably, however, the compound of formula (I) is a compound (I-1), where $R^2$ together with $R^1$ represents a double bond, or is a compound (I-2), where $R^3$ together with $R^1$ represents a double bond, or is a compound (I-3), where $R^4$ together with $R^1$ represents a double bond, or is a mixture of at least two compounds (I-1), (I-2) and (I-3) (where the compound (I-1), the compound (I-2), the compound (I-3) or the mixture of at least two compounds (I-1), (I-2) and (I-3) may contain a minor amount of a compound I in which $R^1$ is OH); or is a compound (I) in which $R^1$ is hydrogen; or is a compound (I) in which $R^1$ is OH; or is a compound (I-1) in which $R^1$ is methoxy. In particular, the compound of formula (I) is a compound (I-1), where $R^2$ together with $R^1$ represents a double bond, or is a compound (I-2), where $R^3$ together with $R^1$ represents a double bond, or is a compound (I-3), where $R^4$ together with $R^1$ represents a double bond, or is a mixture of at least two compounds (I-1), (I-2) and (I-3) (where the compound (I-1), the compound (I-2), the compound (I-3) or the mixture of at least two compounds (I-1), (I-2) and (I-3) may contain a minor amount of a compound I in which $R^1$ is OH); or is a compound (I) in which $R^1$ is hydrogen; or is a compound (I) in which $R^1$ is OH. Specifically, the compound of formula (I) is a compound (I-1), where $R^2$ together with $R^1$ represents a double bond, or is a compound (I-2), where $R^3$ together with $R^1$ represents a double bond, or is a compound (I-3), where $R^4$ together with $R^1$ represents a double bond, or is a mixture of at least two compounds (I-1), (I-2) and (I-3) (where the compound (I-1), the compound (I-2), the compound (I-3) or the mixture of at least two compounds (I-1), (I-2) and (I-3) may contain a minor amount of a compound I in which $R^1$ is OH). The above mixtures are preferably mixtures of double bond isomers, in which X in all compounds (I) contained therein has the same meaning.

In a particular embodiment of the present invention, in compounds of the formula (I), X is O and one of $R^2$, $R^3$, $R^4$ together with $R^1$ represents a double bond.

In a more particular embodiment, the compound of formula (I) is a compound (I-1), where $R^2$ together with $R^1$ represents a double bond and in which X is O, or is a compound (I-2), where $R^3$ together with $R^1$ represents a double bond and in which X is O, or is a compound (I-3), where $R^4$ together with $R^1$ represents a double bond and in which X is O, or is a mixture of at least two compounds (I-1), (I-2) and (I-3) in which X is O. As already said above, the compound (I-1), the compound (I-2), the compound (I-3) or the mixture of at least two compounds (I-1), (I-2) and (I-3) may contain a minor amount of a compound I in which $R^1$ is OH. "Minor amount" means less than 3% by weight, preferably less than 1% by weight, relative to the total weight of the compounds (I-1), (I-2) and (I-3) or a mixture thereof, including the compound I in which $R^1$ is OH.

In an even more particular embodiment, the compound of formula (I) is a compound (I-1), where $R^2$ together with $R^1$ represents a double bond and X is O. In another even more particular embodiment, the compound of formula (I) is a compound (I-2), where $R^3$ together with $R^1$ represents a double bond and X is O. In another even more particular embodiment, the compound of formula (I) is a compound (I-3), where $R^4$ together with $R^1$ represents a double bond and X is O. Specifically, the compound of formula (I) is a compound (I-2) in which X is O.

In yet another even more particular embodiment, the compound of formula (I) is a mixture of at least two compounds (I-1), (I-2) and (I-3), where in each case X is O. More particularly, the mixture contains compounds (I-2) and (I-3) or contains all three compounds (I-1), (I-2) and (I-3), where in each case X is O.

In particular, the mixture contains compounds I-2 and I-3 and optionally also compound I-1, where in each case X is O; where compound I-1 is contained in an amount of from 0 to 10% by weight, compound I-2 is contained in an amount of from 1 to 80% by weight, and compound I-3 is contained in an amount of from 15 to 99% by weight, relative to the total weight of compounds I-1, I-2 and I-3. Specifically, the mixture contains all three compounds (I-1), (I-2) and (I-3), where in each case X is O; where compound I-1 is contained in an amount of from 0.1 to 10% by weight, compound I-2 is contained in an amount of from 1 to 79.9% by weight, and compound I-3 is contained in an amount of from 15 to 99% by weight, relative to the total weight of compounds I-1, I-2 and I-3.

In a specific embodiment, the compound of formula (I) is a binary mixture of compounds (I-2) and (I-3), where in each case X is O and where compound (I-3) predominates, i.e. it is present in an amount of more than 50% by weight, based on the weight of the mixture consisting of compounds (I-2) and (I-3). In particular, it is present in an amount of from 70 to 99% by weight, more particularly from 75 to 98% by weight, specifically from 80 to 95% by weight, and very specifically from 90 to 95% by weight, based on the weight of the mixture consisting of compounds (I-2) and (I-3); the difference to 100% being the compound (I-2).

In a specific embodiment, the compound of formula (I) is a ternary mixture of compounds (I-1), (I-2) and (I-3), where in each case X is O and where compound (I-2) predominates. In particular, it is present in an amount of from 50 to 80% by weight, more particularly from 55 to 75% by weight and specifically from 60 to 70% by weight, based on the weight of the mixture consisting of compounds (I-1), (I-2) and (I-3). Specifically, in the ternary mixture the compound (I-3) is the second most frequent component, and is in particular present in an amount of from 15 to 45% by weight, more particularly from 20 to 40% by weight and specifically from 28 to 39.5% by weight, based on the weight of the mixture consisting of compounds (I-1), (I-2) and (I-3). The compound (I-1) is specifically the minor compound and is in particular present in an amount of from 0.1 to 10% by weight, more particularly from 0.5 to 5% by weight and specifically from 0.5 to 2% by weight, based on the weight of the mixture consisting of compounds (I-1), (I-2) and (I-3). As a matter of course, the percentages of compounds (I-1), (I-2) and (I-3) add to 100%.

In another specific embodiment, the compound of formula (I) is a ternary mixture of compounds (I-1), (I-2) and (I-3), where in each case X is O and where compound (I-3) predominates. In particular, it is present in an amount of from 50 to 90% by weight, more particularly from 70 to 90% by weight and specifically from 75 to 85% by weight, based on the weight of the mixture consisting of compounds (I-1), (I-2) and (I-3). Specifically, in the ternary mixture the compound (I-2) is the second most frequent component, and is in particular present in an amount of from 9 to 45% by weight, more particularly from 9 to 29.5% by weight and specifically from 13 to 24.5% by weight, based on the weight of the mixture consisting of compounds (I-1), (I-2) and (I-3). The compound (I-1) is specifically the minor compound and is in particular present in an amount of from 0.1 to 10% by weight, more particularly from 0.5 to 5% by weight and specifically from 0.5 to 2% by weight, based on the weight of the mixture consisting of compounds (I-1), (I-2) and (I-3). As a matter of course, the percentages of compounds (I-1), (I-2) and (I-3) add to 100%.

Specifically, the mixture contains compounds I-1, I-2 and I-3, where in each case X is O, where compound I-1 is contained in an amount of from 0.5 to 1.5% by weight, compound I-2 is contained in an amount of from 15 to 73.5% by weight, and compound I-3 is contained in an amount of from 25 to 84.5% by weight, relative to the total weight of compounds I-1, I-2 and I-3. As a matter of course, the percentages of compounds (I-1), (I-2) and (I-3) add to 100%.

In another preferred embodiment of the present invention, in compounds of the general formula (I), $R^1$ is hydrogen and X is O (the compound (I) being thus a compound (I-4) in which X is O).

In another preferred embodiment of the present invention, in compounds of the general formula (I), $R^1$ is OH and X is O (the compound (I) being thus a compound (I-5) in which X is O).

In another preferred embodiment of the present invention, in compounds of the general formula (I), $R^1$ is O—$C_1$-$C_4$-alkyl and X is O (the compound (I) being thus a compound (I-6) in which X is O). In particular $R^1$ is O—$C_1$-$C_2$-alkyl (i.e. $R^1$ is methoxy or ethoxy) and X is O. Specifically, $R^1$ is methoxy and X is O.

In another preferred embodiment of the present invention, in compounds of the general formula (I), $R^1$ is O—(C=O)—$R^5$ and X is O (the compound (I) being thus a compound (I-7) in which X is O). Preferably, $R^5$ is $C_1$-$C_4$-alkyl, in particular $C_1$-$C_2$-alkyl, and X is O. Specifically, $R^5$ is methyl (i.e. $R^1$ is acetoxy) and X is O.

More preferably, however, the compound of formula (I) is a compound (I-1), where $R^2$ together with $R^1$ represents a double bond and X is O, or is a compound (I-2), where $R^3$ together with $R^1$ represents a double bond and X is O, or is a compound (I-3), where $R^4$ together with $R^1$ represents a double bond and X is O, or is a mixture of at least two compounds (I-1), (I-2) and (I-3), where in each case and X is O (where the compound (I-1), the compound (I-2), the compound (I-3) or the mixture of at least two compounds (I-1), (I-2) and (I-3) may contain a minor amount of a compound I in which $R^1$ is OH and X is O); or is a compound (I) in which $R^1$ is hydrogen and X is O; or is a compound (I) in which $R^1$ is OH and X is O; or is a compound (I) in which $R^1$ is methoxy and X is O. In particular, the compound of formula (I) is a compound (I-1), where $R^2$ together with $R^1$ represents a double bond and X is O, or is a compound (I-2), where $R^3$ together with $R^1$ represents a double bond and X is O, or is a compound (I-3), where $R^4$ together with $R^1$ represents a double bond and X is O, or is a mixture of at least two compounds (I-1), (I-2) and (I-3), where in each case and X is O (where the compound (I-1), the compound (I-2), the compound (I-3) or the mixture of at least two compounds (I-1), (I-2) and (I-3) may contain a minor amount of a compound I in which $R^1$ is OH and X is O); or is a compound (I) in which $R^1$ is hydrogen and X is O; or is a compound (I) in which $R^1$ is OH and X is O. Specifically, the compound of formula (I) is a compound (I-1), where $R^2$ together with $R^1$ represents a double bond and X is O, or is a compound (I-2), where $R^3$ together with $R^1$ represents a double bond and X is O, or is a compound (I-3), where $R^4$ together with $R^1$ represents a double bond and X is O, or is a mixture of at least two compounds (I-1), (I-2) and (I-3), where in each case X is O (where the compound (I-1), the compound (I-2), the compound (I-3) or the mixture of at least two compounds (I-1), (I-2) and (I-3) may contain a minor amount of a compound I in which $R^1$ is OH and X is O).

In another particular embodiment of the present invention, in compounds of the formula (I), X is S and one of $R^2$, $R^3$, $R^4$ together with $R^1$ represents a double bond.

In another more particular embodiment, the compound of formula (I) is a compound (I-1), where $R^2$ together with $R^1$ represents a double bond and in which X is S, or is a compound (I-2), where $R^3$ together with $R^1$ represents a double bond and in which X is S. or is a compound (I-3), where $R^4$ together with $R^1$ represents a double bond and in which X is S, or is a mixture of at least two compounds (I-1), (I-2) and (I-3) in which X is S. As already said above, the compound (I-1), the compound (I-2), the compound (I-3) or the mixture of at least two compounds (I-1), (I-2) and (I-3) may contain a minor amount of a compound I in which $R^1$ is OH. "Minor amount" means less than 3% by weight, preferably less than 1% by weight, relative to the total weight of the compounds (I-1), (I-2) and (I-3) or a mixture thereof, including the compound I in which $R^1$ is OH.

In another even more particular embodiment, the compound of formula (I) is a compound (I-1), where $R^2$ together with $R^1$ represents a double bond and X is S. In another even more particular embodiment, the compound of formula (I) is a compound (I-2), where $R^3$ together with $R^1$ represents a double bond and X is S. In another even more particular embodiment, the compound of formula (I) is a compound (I-3), where $R^4$ together with $R^1$ represents a double bond and X is S. Specifically, the compound of formula (I) is a compound (I-2) in which X is S.

In yet another particular embodiment, the compound of formula (I) is a mixture of at least two compounds (I-1), (I-2) and (I-3), where in each case X is S. More particularly, the mixture contains compounds (I-2) and (I-3) or contains all three compounds (I-1), (I-2) and (I-3), where in each case X is S.

In particular, the mixture contains compounds I-2 and I-3 and optionally also compound I-1, where in each case X is S; where compound I-1 is contained in an amount of from 0 to 10% by weight, compound I-2 is contained in an amount of from 1 to 80% by weight, and compound I-3 is contained in an amount of from 15 to 99% by weight, relative to the total weight of compounds I-1, I-2 and I-3. Specifically, the mixture contains all three compounds (I-1), (I-2) and (I-3), where in each case X is S; where compound I-1 is contained in an amount of from 0.1 to 10% by weight, compound I-2 is contained in an amount of from 1 to 79.9% by weight, and compound I-3 is contained in an amount of from 15 to 99% by weight, relative to the total weight of compounds I-1, I-2 and I-3.

In a specific embodiment, the compound of formula (I) is a binary mixture of compounds (I-2) and (I-3), where in each case X is S and where compound (I-3) predominates, i.e. it is present in an amount of more than 50% by weight, based on the weight of the mixture consisting of compounds (I-2) and (I-3). In particular, it is present in an amount of from 50 to 99% by weight, more particularly from 55 to 90% by weight and specifically from 55 to 80% by weight, based on the weight of the mixture consisting of compounds (I-2) and (I-3); the difference to 100% being the compound (I-2).

In a specific embodiment, the compound of formula (I) is a ternary mixture of compounds (I-1), (I-2) and (I-3), where in each case X is S and where compound (I-3) predominates. In particular, it is present in an amount of from 50 to 80% by weight, more particularly from 55 to 75% by weight and specifically from 55 to 70% by weight, based on the weight of the mixture consisting of compounds (I-1), (I-2) and (I-3). Specifically, in the ternary mixture the compound (I-2) is the second most frequent component, and is in particular present in an amount of from 10 to 45% by weight, more particularly from 20 to 44.5% by weight and specifically from 25 to 43% by weight, based on the weight of the mixture consisting of compounds (I-1), (I-2) and (I-3). The compound (I-1) is specifically the minor compound and is in particular present in an amount of from 0.1 to 10% by weight, more particularly from 0.5 to 5% by weight and specifically from 0.5 to 2% by weight, based on the weight of the mixture consisting of compounds (I-1), (I-2) and (I-3). As a matter of course, the percentages of compounds (I-1), (I-2) and (I-3) add to 100%.

In another preferred embodiment of the present invention, in compounds of the general formula (I), $R^1$ is hydrogen and X is S (the compound (I) being thus a compound (I-4) in which X is S).

In another preferred embodiment of the present invention, in compounds of the general formula (I), $R^1$ is OH and X is S (the compound (I) being thus a compound (I-5) in which X is S).

In another preferred embodiment of the present invention, in compounds of the general formula (I), $R^1$ is O—$C_1$-$C_4$-alkyl and X is S (the compound (I) being thus a compound (I-6) in which X is S). In particular $R^1$ is O—$C_1$-$C_2$-alkyl (i.e. $R^1$ is methoxy or ethoxy) and X is S. Specifically, $R^1$ is methoxy and X is S.

In another preferred embodiment of the present invention, in compounds of the general formula (I), $R^1$ is O—(C=O)—$R^5$ and X is S (the compound (I) being thus a compound (I-7) in which X is S). Preferably, $R^5$ is $C_1$-$C_4$-alkyl, in particular $C_1$-$C_2$-alkyl, and X is S. Specifically, $R^5$ is methyl (i.e. $R^1$ is acetoxy) and X is S.

More preferably however, the compound of formula (I) is a compound (I-1), where $R^2$ together with $R^1$ represents a double bond and X is S, or is a compound (I-2), where $R^3$ together with $R^1$ represents a double bond and X is S, or is a compound (I-3), where $R^4$ together with $R^1$ represents a double bond and X is S, or is a mixture of at least two compounds (I-1), (I-2) and (I-3), where in each case and X is S (where the compound (I-1), the compound (I-2), the compound (I-3) or the mixture of at least two compounds (I-1), (I-2) and (I-3) may contain a minor amount of a compound I in which $R^1$ is OH and X is S); or is a compound (I) in which $R^1$ is hydrogen and X is S; or is a compound (I) in which $R^1$ is OH and X is S. In particular, the compound of formula (I) is a compound (I-1), where $R^2$ together with $R^1$ represents a double bond and X is S, or is a compound (I-2), where $R^3$ together with $R^1$ represents a double bond and X is S, or is a compound (I-3), where $R^4$ together with $R^1$ represents a double bond and X is S, or is a mixture of at least two compounds (I-1), (I-2) and (I-3), where in each case and X is S (where the compound (I-1), the compound (I-2), the compound (I-3) or the mixture of at least two compounds (I-1), (I-2) and (I-3) may contain a minor amount of a compound I in which $R^1$ is OH and X is S); or is a compound (I) in which $R^1$ is OH and X is S. Specifically, the compound of formula (I) is a compound (I-1), where $R^2$ together with $R^1$ represents a double bond and X is S, or is a compound (I-2), where $R^3$ together with $R^1$ represents a double bond and X is S, or is a compound (I-3), where $R^4$ together with $R^1$ represents a double bond and X is S, or is a mixture of at least two compounds (I-1), (I-2) and (I-3), where in each case X is S (where the compound (I-1), the compound (I-2), the compound (I-3) or the mixture of at least two compounds (I-1), (I-2) and (I-3) may contain a minor amount of a compound I in which $R^1$ is OH and X is S).

The compounds of formula (I), the stereoisomers thereof, the mixtures of stereoisomers thereof and mixtures of two or more different compounds (I) are useful as aroma chemicals.

The term "aroma chemical" denotes a substance which is used to obtain a sensory impression, to be more precise an olfactory or flavor impression, in particular a fragrance or flavor impression. The term "olfactory" denotes an odor impression without any positive or negative judgement, while the term "fragrance" (also termed "perfume" or "scent") is connected to an odor impression which is generally felt as pleasant. A flavor induces a taste impression.

"Pleasant odor", "pleasant odor impression", "pleasant odiferous properties", "odor impression felt as pleasant" and similar terms are hedonistic expressions which describe the niceness and conciseness of an odor impression conveyed by an aroma chemical. The more general hedonistic expressions "advantageous sensory properties" or "advantageous organoleptic properties" describe the niceness and conciseness of an organoleptic impression conveyed by an aroma chemical. In terms of the present invention, the terms "organoleptic" and "sensory" relate to olfactory or flavor properties. "Niceness" and "conciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typically tart apple can also be concise. If both reactions arise upon smelling the substance, in the example thus a nice and concise apple odor, then this substance has particularly advantageous sensory properties.

The term "odor-intensive substances" refers to substances or aroma chemicals exhibiting intense odor impressions. Intense odor impressions are to be understood as meaning those properties of aroma chemicals which permit a striking perception even in very low gas space concentrations. The intensity can be determined via a threshold value determination. A threshold value is the concentration of a substance in the relevant gas space at which an odor impression can just still be perceived by a representative test panel, although it no longer has to be defined. A substance class which probably belongs to the most odor-intensive known substance classes, i.e. has very low odor threshold values, are thiols, whose threshold value is often in the ppb/m$^3$ range.

Preferably, the compound of formula (I) or a mixture thereof or a stereoisomer thereof or a mixture of stereoisomers thereof as defined above is used for imparting an olfactory impression. In particular, the compound of formula (I) or a mixture thereof or a stereoisomer thereof or a mixture of stereoisomers thereof as defined above is used as a fragrance.

In particular, a mixture of the above-described compounds (I-1), (I-2) and (I-3), wherein X is O, or a mixture of stereoisomers thereof is used to impart a galbanum, herbal, smoky, leather note; or is used to produce a scent with a galbanum, herbal, smoky, leather note. Specifically, compounds (I-1), (I-2) and (I-3), wherein X is O, are present in a weight ratio of ca. 1:65.5:33.5.

In particular, a mixture of the above-described compounds (I-1), (I-2) and (I-3), wherein X is O, or a mixture of stereoisomers thereof is used to impart a herbal, smoky, spicy, nutmeg, galbanum, leather, oakmoss note; or is used to produce a scent with a herbal, smoky, spicy, nutmeg, galbanum, leather, oakmoss note. Specifically, compounds (I-1), (I-2) and (I-3), wherein X is O, are present in a weight ratio of ca. 1:19.5:79.5.

In particular, a mixture of the above-described compounds (I-2) and (I-3), wherein X is O, or a mixture of stereoisomers thereof is used to impart a spicy, nutmeg, smoky, tobacco, leather, phenol note; or is used to produce a scent with a spicy, nutmeg, smoky, tobacco, leather, phenol note. Specifically, compounds (I-2) and (I-3), wherein X is O, are present in a weight ratio of 7:92.

In particular, compound (I-2), wherein X is O, or a stereoisomer thereof or a mixture of stereoisomers thereof is used to impart a root, galbanum, leather, spicy note; or is used to produce a scent with a root, galbanum, leather, spicy note.

In particular, the compound (I) wherein $R^1$ is H and X is O (and of course $R^2$, $R^3$ and $R^4$ are H) (=a compound (I-4) wherein X=O) or a stereoisomer thereof or a mixture of stereoisomers thereof is used to impart a smoked, lime, hickory, green, sweet note; or is used to produce a scent with a smoked, lime, hickory, green, sweet note.

In particular, the compound (I) wherein $R^1$ is OH and X is O (and of course $R^2$, $R^3$ and $R^4$ are H) (=a compound (I-5) wherein X=O) or a stereoisomer thereof or a mixture of stereoisomers thereof is used to impart a galbanum, floral note; or is used to produce a scent with a galbanum, floral note.

In particular, the compound (I) wherein $R^1$ is OCH$_3$ and X is O (and of course $R^2$, $R^3$ and $R^4$ are H) or a stereoisomer thereof or a mixture of stereoisomers thereof is used to impart a watery, melon, slightly bitter note; or is used to produce a scent with a watery, melon, slightly bitter note.

In particular, a mixture of the above-described compounds (I-1), (I-2) and (I-3), wherein X is S, or a mixture of stereoisomers thereof is used to impart a green, herbal, chives, woody note; or is used to produce a scent with a green, herbal, chives, woody note. Specifically, compounds (I-1), (I-2) and (I-3), wherein X is S, are present in a weight ratio of 1:39:60.

In particular, the compound (I) wherein $R^1$ is OH and X is S (and of course $R^2$, $R^3$ and $R^4$ are H) (=a compound (I-5) wherein X=S) or a stereoisomer thereof or a mixture of stereoisomers thereof is used to impart a beer, burnt note; or is used to produce a scent with a beer, burnt note.

The compounds (I), the mixtures thereof, the stereoisomers thereof or the stereoisomer mixtures thereof are generally used in a ready-to-use composition, in particular in a fragranced ready-to-use composition. "Fragranced ready-to-use composition", as used herein, refers to a ready-to-use composition which predominately induces a pleasant odor impression.

Fragranced ready-to-use compositions are for example compositions used in personal care, in home care, in industrial applications as well as compositions used in other applications, such as pharmaceutical compositions or crop protection compositions.

Preferably, the compounds (I), the mixtures thereof, the stereoisomers thereof or the stereoisomer mixtures thereof are used in a composition selected from the group consisting of perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions and crop protection compositions. The compounds (I), the stereoisomers thereof, the stereoisomer mixtures thereof or the double bond isomers thereof are used as an aroma chemical, preferably as a fragrance, in the above compositions.

In particular, a mixture of the above-described compounds (I-1), (I-2) and (I-3), wherein X is O, or a mixture of stereoisomers thereof is used to impart a galbanum, herbal, smoky, leather note to the above-listed compositions. Specifically, compounds (I-1), (I-2) and (I-3), wherein X is O, are present in a weight ratio of ca. 1:65.5:33.5.

In particular, a mixture of the above-described compounds (I-1), (I-2) and (I-3), wherein X is O or a mixture of stereoisomers thereof is used to impart a herbal, smoky, spicy, nutmeg, galbanum, leather, oakmoss note to the above-listed compositions. Specifically, compounds (I-1), (I-2) and (I-3), wherein X is O, are present in a weight ratio of ca. 1:19.5:79.5.

In particular, a mixture of the above-described compounds (I-2) and (I-3), wherein X is O, or a mixture of stereoisomers thereof is used to impart a spicy, nutmeg, smoky, tobacco, leather, phenol note to the above-listed compositions. Specifically, compounds (I-2) and (I-3), wherein X is O, are present in a weight ratio of 7:92.

In particular, compound (I-2), wherein X is O, or a stereoisomer thereof or a mixture of stereoisomers thereof is used to impart a root, galbanum, leather, spicy note to the above-listed compositions.

In particular, the compound (I) wherein $R^1$ is H and X is O (and of course $R^2$, $R^3$ and $R^4$ are H) (=a compound (I-4) wherein X=O) or a stereoisomer thereof or a mixture of stereoisomers thereof is used to impart a smoked, lime, hickory, green, sweet note to the above-listed compositions.

In particular, the compound (I) wherein $R^1$ is OH and X is O (and of course $R^2$, $R^3$ and $R^4$ are H) (=a compound (I-5) wherein X=O) or a stereoisomer thereof or a mixture of stereoisomers thereof is used to impart a galbanum, floral note to the above-listed compositions.

In particular, the compound (I) wherein $R^1$ is $OCH_3$ and X is O (and of course $R^2$, $R^3$ and $R^4$ are H) or a stereoisomer thereof or a mixture of stereoisomers thereof is used to impart a watery, melon, slightly bitter note to the above-listed compositions.

In particular, a mixture of the above-described compounds (I-1), (I-2) and (I-3), wherein X is S, or a mixture of stereoisomers thereof is used to impart a green, herbal, chives, woody note to the above-listed compositions. Specifically, compounds (I-1), (I-2) and (I-3), wherein X is S, are present in a weight ratio of 1:39:60.

In particular, the compound (I) wherein $R^1$ is OH and X is S (and of course $R^2$, $R^3$ and $R^4$ are H) (=a compound (I-5) wherein X=S) or a stereoisomer thereof or a mixture of stereoisomers thereof is used to impart a beer, burnt note to the above-listed compositions.

Details to the above-listed compositions are given below.

In addition to the olfactory properties, the compounds (I), the mixtures thereof, the stereoisomers thereof or the stereoisomer mixtures thereof exhibit advantageous secondary properties.

For example, they can provide better sensory profiles as a result of synergistic effects with other fragrances, which means that they can provide a booster effect for other fragrances. They are therefore suitable as boosters for other fragrances.

Accordingly, another aspect of the invention relates to the use of the compounds (I), the mixtures thereof, the stereoisomers thereof or the stereoisomer mixtures thereof for modifying the scent character of a fragranced composition; and specifically to the use as a booster for other fragrances.

Booster effect means that the substances enhance and intensify in perfumery formulations the overall impression of the mixture. In the mint range, for example, it is known that menthyl methyl ether intensifies the perfumery or taste mixtures of peppermint oils and particularly in top notes brings about a considerably more intensive and more complex perception although the ether itself, being a pure substance, develops no particular intensive odor at all. In fragrance applications, Hedione® (methyl dihydrojasmonate), which as a pure substance only exhibits a light floral jasmin-note, reinforces diffusion, freshness and volume of a perfume composition as an odor booster. Booster effects are particularly desired when top-note-characterized applications are required, in which the odor impression is to be conveyed particularly quickly and intensively, for example in deodorants, air fresheners or in the taste sector in chewing gums.

To achieve such a booster effect, the compounds (I), the mixtures thereof, the stereoisomers thereof or the stereoisomer mixtures thereof are generally used in an amount of 0.1-20% by weight, preferably in an amount of 0.5 to 5% by weight, in particular in an amount of from 0.6 to 3% by weight, based on the total weight of the fragrance mixture.

Furthermore, the compounds (I), the mixtures thereof, the stereoisomers thereof or the stereoisomer mixtures thereof can have further positive effects on the composition in which they are used. For example, they can enhance the overall performance of the composition into which they are incorporated, such as the stability, e.g. the formulation stability, the extendability or the staying power of the composition.

In another aspect, the present invention relates to an aroma chemical composition comprising the compounds (I), mixtures thereof, the stereoisomers thereof or stereoisomer mixtures thereof. The term "aroma chemical composition", as used herein, refers to a composition which induces a pleasant odor impression.

Preferably, the aroma chemical composition comprises
a compound of formula (I) or a mixture thereof [i.e. mixture of different compounds (I)], or a stereoisomer thereof or a stereoisomer mixture thereof; and
at least one further aroma chemical and/or at least one non-aroma chemical carrier, where the non-aroma chemical carrier is in particular selected from the group consisting of surfactants, oil components (emollients) and solvents.

The further aroma chemical is of course different from the compound of formula (I) or its stereoisomers or mixtures of its stereoisomers.

By virtue of their physical properties, the compound of formula (I), the mixtures thereof, the stereoisomers thereof or the stereoisomer mixtures thereof have particularly good, virtually universal solvent properties for other fragrances and other customary ingredients in fragranced ready to use compositions such as, in particular, perfume compositions. Therefore, they are well combinable with other aroma chemicals, allowing, in particular, the creation of perfume compositions having novel advantageous sensory profiles. Especially, as already explained above, they can provide a booster effect for other fragrances.

Accordingly, in one preferred embodiment, the aroma chemical composition comprises the compound of formula (I) or a mixture thereof, or a stereoisomer thereof or a stereoisomer mixture thereof as defined above; and at least one further aroma chemical.

The further aroma chemical can for example be one, preferably 2, 3, 4, 5, 6, 7, 8 or further aroma chemicals, selected from the group consisting of:

Geranyl acetate (3,7-Dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60% by weight) (Hedione[9], Hedione HC[9]), 4,6,6,7,8,8-hexamethyl-1,3,4,6,7,8-hexahydro-cyclopenta[g]benzopyran (Galaxolid[3]), tetrahydrolinalool (3,7- dimethyloctan-3-ol), ethyllinalool, benzyl salicylate, 2-methyl-3-(4-tert-butylphenyl)propanal (Lysmeral[2a]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melonal[2]), borneol, 3-(3-isopropylphenyl) butanal (Florhydral[2]), 2-methyl-3-(3,4-methylenedioxyphenyl)-propanal (Helional[3]), 3-(4-ethylphenyl)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70% by weight) or more and 2,5,5-trimethyl-1,2,3,4,4a,5,6,7-octahydronaphthalen-2-ol (Ambrinol S[1]). Within the context of the present invention, the aforementioned aroma chemical(s) are accordingly preferably combined with the compound of formula (I) or a stereoisomer thereof or a mixture of stereoisomers thereof or a double bond isomer thereof as defined above.

A further embodiment of the invention relates to a composition comprising the compound of formula (I) or a mixture thereof, or a stereoisomer thereof or a stereoisomer mixture thereof as defined above and at least one further aroma chemical selected from the group consisting of methyl benzoate, benzyl acetate, geranyl acetate, 2-isobutyl-4-methyltetrahydro-2H-pyran-4-ol and linalool.

A further embodiment of the invention relates to a composition comprising the compound of formula (I) or a mixture thereof, or a stereoisomer thereof or a stereoisomer mixture thereof as defined above and 2-isobutyl-4-methyltetrahydro-2H-pyran-4-ol.

A further embodiment of the invention relates to a composition comprising the compound of formula (I) or a mixture thereof, or a stereoisomer thereof or a stereoisomer mixture thereof as defined above and methyl benzoate.

Where trade names are given above, these refer to the following sources:
[1] trade name of Symrise GmbH, Germany;
[2] trade name of Givaudan AG, Switzerland;
[2a] trade name of BASF SE, Germany;
[3] trade name of International Flavors & Fragrances Inc., USA;
[5] trade name of Danisco Seillans S.A., France;
[9] trade name of Firmenich S.A., Switzerland;
[10] trade name of PFW Aroma Chemicals B.V., the Netherlands.

Further aroma chemicals with which the compound of formula (I) or a mixture thereof, or a stereoisomer thereof or a stereoisomer mixture thereof as defined above can be combined e.g. to give a composition according to the invention can be found e.g. in S. Arctander, Perfume and Flavor Chemicals, Vol. I and II, Montclair, N. J., 1969, self-published or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom; individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal;

dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl-acetals of geranial, neral, 7-hydroxy-3,7-dimethyloctanal;

the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methano-naphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclo-dodecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo-[10.1.0]trideca-4,8-diene; roseoxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclo-hexadecen-1-one; 7-cyclohexadecen-1-one; (7/8)-cyclohexadecen-1-one; 9-cyclo-heptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)-ethanone; 2-benzofuranylethanone; (3-methyl-2-benzofuranyl)ethanone; benzo-phenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropyl-pyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Advantageous are combinations with aroma chemicals with a sweet note, such as vanillin, 2,5-dimethyl-4-hydroxy-2H-furan-3-one (furaneol) or 3-hydroxy-2-methyl-4H-pyran-4-one (maltol), of the sweet note of which is boosted by the compound (I) or its stereoisomers or its double bond isomers.

A further aspect of the invention is directed to a composition comprising the compound of formula (I) or a mixture thereof, or a stereoisomer thereof or a stereoisomer mixture thereof as defined above and at least one component selected from the group consisting of surfactants, emollients (oil component) and solvents.

One embodiment of the invention is directed to a composition comprising the compound of formula (I) or a mixture thereof, or a stereoisomer thereof or a stereoisomer mixture thereof as defined above and at least one solvent.

In the context of the present invention, a "solvent" serves for the dilution of the compound of formula (I) or a mixture thereof, or a stereoisomer thereof or a stereoisomer mixture thereof as defined above to be used according to the invention without having its own odiferous properties. Some solvents have fixing properties at the same time.

The one or more solvent(s) can be present in the composition from 0.01 to 99% by weight based on the composition. In a preferred embodiment of the invention, the composition comprise 0.1 to 90 weight %, preferably 0.5 to 80 weight % of solvent(s) based on the composition. The amount of solvent(s) can be chosen depending on the composition. In one embodiment of the invention, the composition comprises 0.05 to 10 weight %, preferably 0.1 to 5 weight %, more preferably 0.2 to 3 weight % based on the composition. In one embodiment of the invention, the composition comprises 20 to 70 weight %, preferably 25 to 50 weight % of solvent(s) based on the composition.

Preferred solvents are ethanol, isopropanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB).

Especially preferred solvents are selected from the group consisting of ethanol, propylene glycol, dipropylene glycol, triethyl citrate, benzyl benzoate and isopropyl myristate.

In a preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

According to a further aspect, the compound of formula (I), mixtures thereof, stereoisomers thereof, or mixtures of stereoisomers thereof are suitable for use in surfactant-containing compositions. According to their characteristic scent profiles, they can especially be used for the perfuming of surfactant-containing compositions such as, for example, cleaners (in particular laundry care products and all-purpose cleaners).

One embodiment of the invention is therefore directed to a composition comprising the compound of formula (I) or a mixture thereof, or a stereoisomer thereof or a stereoisomer mixture thereof as defined above and at least one surfactant.

The surfactant(s) may be selected from anionic, non-ionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in a quantity of 0 to 40% by weight, preferably 0 to 20% by weight, more preferably 0.1 to 15% by weight, and particularly 0.1 to 10% by weight, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COOH$^{(-)}$ or —SO$_3^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a C8 to C18 alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear C12-8 alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising the compound of formula (I) or a mixture thereof, or a stereoisomer thereof or a stereoisomer mixture thereof as defined above and at least one oil component.

The oil components are typically present in a total quantity of 0.1 to 80, preferably 0.5 to 70, more preferably 1 to 60, even more preferably 1 to 50% by weight, in particular 1 to 40% by weight, more particularly 5 to 25% by weight and specifically 5 to 15% by weight based on the composition.

The oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkyl-hydroxycarboxylic acids with linear or branched $C_6$-$C_{22}$-fatty alcohols, more especially dioctyl malate, esters of linear and/or branched fatty acids with polyhydric alcohols (for example propylene glycol, dimer dial or trimer triol), triglycerides based on $C_6$-$C_{10}$-fatty acids, liquid mono-, di- and triglyceride mixtures based on $C_6$-$C_{18}$-fatty acids, esters of $C_6$-$C_{22}$-fatty alcohols and/or Guerbet alcohols with aromatic carboxylic acids, more particularly benzoic acid, esters of dicarboxylic acids with polyols containing 2 to 10 carbon atoms and 2 to 6 hydroxyl groups, vegetable oils, branched primary alcohols, substituted cyclohexanes, linear and branched $C_6$-$C_{22}$-fatty alcohol carbonates such as, for example, dicaprylyl carbonate (Cetiol@ CC), Guerbet carbonates based on fatty alcohols containing 6 to 18 and preferably 8 to 10 carbon atoms, esters of benzoic acid with linear and/or branched $C_6$ to $C_{22}$-alcohols (for example Finsolv® TN), linear or branched, symmetrical or nonsymmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

The compounds of formula (I), the mixtures thereof, the stereoisomers thereof or the mixtures of stereoisomers thereof as defined above can be used in a wide range of aroma chemical compositions. The olfactory properties, the substance properties (such as solubility in customary solvents and compatibility with further customary constituents of such compositions), as well as the toxicological acceptability of the compounds of formula (I), the stereoisomers thereof, the mixtures of stereoisomers thereof or the double bond isomers thereof underline their particular suitability for the stated use purposes and compositions.

Suitable aroma chemical compositions are for example perfume compositions, body care compositions, products for oral and dental hygiene, hygiene articles, cleaning compositions, textile detergent compositions, compositions for scent dispensers, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Parfum.

Body care compositions include cosmetic compositions, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products such as e.g. hairsprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams, products of decorative cosmetics such as e.g. eye-liners, eye-shadows, nail varnishes, make-ups, lipsticks and mascara.

Products for oral and dental hygiene include for example toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing detergents both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, softgels, gelcaps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the managing of plant diseases, weeds and other pests (both vertebrate and invertebrate) that damage agricultural crops and forestry.

The compositions according to the invention can further comprise one or more substances, such as, for example: preservatives, abrasives, anti-acne agents, agents to combat skin aging, antibacterial agents, anti-cellulite agents, antidandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, deodorizing agents, antiperspirants, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyes, color-protection agents, pigments, anticorrosives, polyols, surfactants, electrolytes, organic solvents or silicone derivatives.

The compounds of formula (I), the mixtures thereof, the stereoisomers thereof and the mixtures of stereoisomers thereof as defined above, as well as the aroma chemical compositions according to the invention comprising them can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the compound of formula (I), its stereoisomer, the mixtures of its stereoisomers as defined above and composition obtainable by the above method of the invention, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting the compound of formula (I), its stereoisomer, the mixtures of its stereoisomers as defined above or the composition obtainable by the above method of the invention with a suitable wax-like substance and by extrusion with subsequent solidification, optionally in a suitable solvent, e.g. isopropanol.

Generally, the total amount of the compounds of formula (I), the mixtures thereof, the stereoisomers thereof or the mixture of stereoisomers thereof in the aroma chemical compositions according to the present invention is typically adapted to the particular intended use or the intended application and can, thus, vary over a wide range. As a rule, the customary standard commercial amounts for scents are used.

The compositions according to the invention can comprise the compounds of formula (I), the mixtures thereof, the stereoisomers thereof or the mixture of stereoisomers thereof as defined above in an overall amount of from 0.001 to 99.9% by weight, preferably from 0.01 to 90% by weight, more preferably from 0.05 to 80%, in particular from 0.1 to 60% by weight, more particularly from 0.1 to 40% by weight, e.g. from 0.1 to 10% by weight or 0.1 to 15% by weight, based on the total weight of the composition.

In one embodiment of the invention, the compositions comprise the compounds of formula (I), the mixtures thereof, the stereoisomers thereof or the mixture of stereoisomers thereof as defined above in an overall amount of from 0.001 to 5 weight %, preferably from 0.01 to 2 weight % based on the total weight of the composition.

A further embodiment of the invention is directed to a method of preparing an aroma chemical composition, in particular a fragranced composition, especially a fragranced ready-to-use composition, comprising incorporating at least one compound of formula (I), a mixture thereof, a stereoisomer thereof or a mixture of stereoisomers thereof into the target composition, e.g. a ready-to-use composition, resulting in an aroma chemical composition, in particular in a fragranced composition, especially in a fragranced ready-to-use composition. Alternatively, the invention is directed to a method of preparing an aroma chemical composition, in particular a fragranced composition, especially a fragranced ready-to-use composition, comprising mixing at least one compound of formula (I), a mixture thereof, a stereoisomer thereof or a mixture of stereoisomers thereof with at least one aroma chemical different from compounds (I) and/or with at least one non-aroma chemical carrier. Suitable and preferred aroma chemicals different from compounds (I) and non-aroma chemical carriers are described above.

For example, the method can be carried out by mixing at least one compound of formula (I), a stereoisomer thereof or a mixture of stereoisomers thereof, as defined above, and at least one further compound selected from the group consisting of aroma chemicals different from compounds (I) and non-aroma chemical carriers.

The invention is also directed to a method for modifying the scent character of an aroma chemical composition, in particular of a fragranced composition, especially of a fragranced ready-to-use composition, comprising incorporating at least one compound of formula (I), a mixture thereof, a stereoisomer thereof or a mixture of stereoisomers thereof into an aroma chemical composition, in particular into a fragranced composition, especially into a fragranced ready-to-use composition.

In particular, the invention is directed to a method of preparing a perfume composition, body care composition, product for oral and dental hygiene, hygiene article, cleaning composition, textile detergent composition, composition for scent dispensers, food, food supplement, pharmaceutical composition or crop protection composition, comprising including the compounds of formula (I), the mixtures thereof, the stereoisomers thereof or the mixture of stereoisomers thereof as defined above or in a perfume composition, body care composition, product for oral and dental hygiene, hygiene article, cleaning composition, textile detergent composition, composition for scent dispensers, food, food supplement, pharmaceutical composition or crop protection composition.

In one embodiment the invention is directed to a method for imparting a galbanum, herbal, smoky, leather note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein X is O, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-2) and (I-3), wherein X is O, are present in a weight ratio of ca. 1:65.5:33.5.

In another embodiment the invention is directed to a method for imparting a herbal, smoky, spicy, nutmeg, galbanum, leather, oakmoss note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein X is O, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition.

Specifically, compounds (I-1), (I-2) and (I-3), wherein X is O, are present in a weight ratio of ca. 1:19.5:79.5.

In another embodiment the invention is directed to a method for imparting a spicy, nutmeg, smoky, tobacco, leather, phenol note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-2) and (I-3), wherein X is O, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-2) and (I-3), wherein X is O, are present in a weight ratio of 7:92.

In another embodiment the invention is directed to a method for imparting a root, galbanum, leather, spicy note to a perfume composition, body care composition, product for oral and dental hygiene, hygiene article, cleaning composition, textile detergent composition, composition for scent dispensers, food, food supplement, pharmaceutical composition or crop protection composition, which comprises including the compound (I-2), wherein X is O, or a stereoisomer thereof or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition.

In another embodiment the invention is directed to a method for imparting a smoked, lime, hickory, green, sweet note to a perfume composition, body care composition, product for oral and dental hygiene, hygiene article, cleaning composition, textile detergent composition, composition for scent dispensers, food, food supplement, pharmaceutical composition or crop protection composition, which comprises including the compound (I) wherein $R^1$ is H and X is O (and of course $R^2$, $R^3$ and $R^4$ are H) (=a compound (I-4) wherein X=O) or a stereoisomer thereof or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition.

In another embodiment the invention is directed to a method for imparting a galbanum, floral note to a perfume composition, body care composition, product for oral and dental hygiene, hygiene article, cleaning composition, textile detergent composition, composition for scent dispensers, food, food supplement, pharmaceutical composition or crop protection composition, which comprises including the compound of formula (I) wherein $R^1$ is OH and X is O (and of course $R^2$, $R^3$ and $R^4$ are H) (=a compound (I-5) wherein X=O) or a stereoisomer thereof or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition.

In another embodiment the invention is directed to a method for imparting a watery, melon, slightly bitter note to a perfume composition, body care composition, product for oral and dental hygiene, hygiene article, cleaning composition, textile detergent composition, composition for scent dispensers, food, food supplement, pharmaceutical composition or crop protection composition, which comprises including the compound of formula (I) wherein $R^1$ is $OCH_3$ and X is O (and of course $R^2$, $R^3$ and $R^4$ are H) or a stereoisomer thereof or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition.

In another embodiment the invention is directed to a method for imparting a green, herbal, chives, woody note to a perfume composition, body care composition, product for oral and dental hygiene, hygiene article, cleaning composition, textile detergent composition, composition for scent dispensers, food, food supplement, pharmaceutical composition or crop protection composition, which comprises including a mixture of the above-described compounds (I-1), (I-2) and (I-3), wherein X is S, or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition. Specifically, compounds (I-1), (I-2) and (I-3), wherein X is S, are present in a weight ratio of 1:39:60.

In another embodiment the invention is directed to a method for imparting a beer, burnt note to a perfume composition, body care composition, product for oral and dental hygiene, hygiene article, cleaning composition, textile detergent composition, composition for scent dispensers, food, food supplement, pharmaceutical composition or crop protection composition, which comprises including the compound of formula (I) wherein $R^1$ is OH and X is S (and of course $R^2$, $R^3$ and $R^4$ are H) (=a compound (I-5) wherein X=S) or a stereoisomer thereof or a mixture of stereoisomers thereof in a perfume composition, body care composition, product for oral and dental hygiene, hygiene article, cleaning composition, textile detergent composition, composition for scent dispensers, food, food supplement, pharmaceutical composition or crop protection composition.

In a further aspect, the invention relates to a compound of the general formula (I.a)

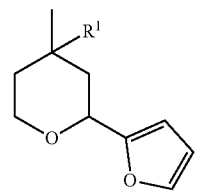

(I.a)

wherein
R$^1$ is hydrogen, OH, O—C$_1$-C$_4$-alkyl or O—(C=O)—R$^5$,
wherein R$^5$ is selected from the group consisting of hydrogen and C$_1$-C$_4$-alkyl;
a mixture thereof, a stereoisomer thereof or a mixture of stereoisomers thereof.

In particular, in compounds (I.a) R$^1$ is selected from the group consisting of hydrogen, OH, methoxy, ethoxy and acetoxy. More particularly, R$^1$ is selected from the group consisting of hydrogen, OH and methoxy. Specifically, R$^1$ is hydrogen or OH.

In an alternative particular embodiment of compounds (I.a) R$^1$ is selected from the group consisting of OH, O—C$_1$-C$_4$-alkyl and O—(C=O)—R$^5$; preferably from OH and O—C$_1$-C$_4$-alkyl; more preferably from OH, methoxy and ethoxy, and in particular from OH and methoxy.

In a further aspect, the invention relates to a compound of the general formula (I.b)

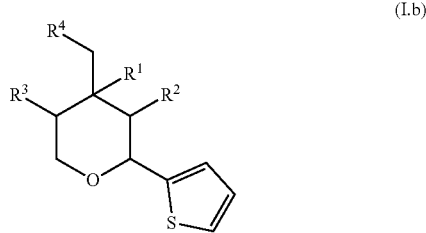

(I.b)

wherein
R$^1$ is hydrogen, OH, O—C$_1$-C$_4$-alkyl or O—(C=O)—R$^5$,
R$^2$, R$^3$, R$^4$ are hydrogen;
or one of R$^2$, R$^3$, R$^4$ together with R$^1$ represents a double bond;
R$^5$ is selected from the group consisting of hydrogen and C$_1$-C$_4$-alkyl;
a mixture thereof, a stereoisomer thereof or a mixture of stereoisomers thereof.

Preferably, in compounds (I.b), R$^2$ together with R$^1$ represents a double bond, or R$^3$ together with R$^1$ represents a double bond, or R$^4$ together with R$^1$ represents a double bond, or compound (I.b) is a mixture of at least two such compounds; or in compounds (I.b), R$^1$ is hydrogen or OH. In particular, in compounds (I.b), R$^2$ together with R$^1$ represents a double bond, or R$^3$ together with R$^1$ represents a double bond, or R$^4$ together with R$^1$ represents a double bond, or compound (I.b) is a mixture of at least two such compounds; or in compounds (I.b), R$^1$ is OH. Specifically, in compounds (I.b), R$^2$ together with R$^1$ represents a double bond, or R$^3$ together with R$^1$ represents a double bond, or R$^4$ together with R$^1$ represents a double bond, or compound (I.b) is a mixture of at least two such compounds. The compounds (I.b), in which R$^2$ together with R$^1$ represents a double bond, or R$^3$ together with R$^1$ represents a double bond, or R$^4$ together with R$^1$ represents a double bond or the mixture of at least two such compounds may contain minor amounts of compound (I.b) in which R$^1$ is OH.

In a further aspect, the invention relates to a mixture of at least two compounds of formula (I) as defined above.

In particular, the mixture is a mixture of a least two compounds I-1, I-2 and I-3, where in compound I-1, R$^2$ together with R$^1$ represents a double bond, in compound I-2, R$^3$ together with R$^1$ represents a double bond and in compound I-3, R$^4$ together with R$^1$ represents a double bond. In such mixtures, X in all compounds I-1, I-2 and I-3 contained in the mixture preferably has the same meaning. Preferably, the mixture of I-1, I-2 and/or I-3 is a mixture containing compound I-2 and one or both of compounds I-1 and I-3; or is a mixture containing compounds I-1 and I-2 and optionally also compound I-3; or is a mixture containing compounds I-2 and I-3 and optionally also compound I-1; or is a mixture containing compounds I-1, I-2 and I-3; and is specifically a mixture containing compounds I-1 and I-2, where preferably X in all compounds I-1, I-2 and I-3 contained in the mixture has the same meaning.

In another specific embodiment, the mixture contains compounds I-2 and I-3 and optionally also compound I-1. Specifically, the mixture contains compounds I-2 and I-3 and optionally also compound I-1, where compound I-1 is contained in an amount of from 0 to 10% by weight, compound I-2 is contained in an amount of from 1 to 80% by weight, and compound I-3 is contained in an amount of from 15 to 99% by weight, relative to the total weight of compounds I-1, I-2 and I-3, where preferably X in all compounds I-1, I-2 and I-3 contained in the mixture has the same meaning. More specifically, the mixture contains compounds I-1, I-2 and I-3, where compound I-1 is contained in an amount of from 0.1 to 10% by weight, compound I-2 is contained in an amount of from 1 to 79.9% by weight, and compound I-3 is contained in an amount of from 15 to 99% by weight, relative to the total weight of compounds I-1, I-2 and I-3, where preferably X in all compounds I-1, I-2 and I-3 contained in the mixture has the same meaning. Even more specifically, the mixture contains compounds I-1, I-2 and I-3, where compound I-1 is contained in an amount of from 0.5 to 1.5% by weight, compound I-2 is contained in an amount of from 15 to 73.5% by weight, and compound I-3 is contained in an amount of from 25 to 84.5% by weight, relative to the total weight of compounds I-1, I-2 and I-3, where preferably X in all compounds I-1, I-2 and I-3 contained in the mixture has the same meaning.

In a specific embodiment of the mixture of the invention, X is S.

The compounds of the formula (I) can be prepared by the methods as described in the below schemes or in the synthesis descriptions of the working examples, or by standard methods of organic chemistry. The substituents, variables and indices are as defined above for formula (I), if not otherwise specified.

To be more precise, the compounds (I) can be prepared by standard methods for preparing cyclic ethers, e.g. by a Prins reaction including reacting isoprenol (3-methylbut-3-en-1-ol) 1 with furfural (X=O) or thiophene carbaldehyde (X=S) 2, as shown in scheme 1 below. The reaction of 1 with 2 is generally carried out under acidic conditions, using for example hydrochloric acid, sulfuric acid, acetic acid, trifluoroacetic acid, methanesulfonic acid or p-toluene sulfonic acid or using a polymeric acid, such as a strongly acidic cation exchanger. The term "strongly acidic cationic exchanger" refers to a cationic exchanger in the H$^+$ form which has strongly acidic groups. The strongly acidic groups are generally sulfonic acid groups; they are generally bonded to a polymer matrix, which can be e.g. gel-like and/or macroporous. Preference is given to styrene (co) polymers containing sulfonic acid groups, specifically to styrene-divinyl benzene copolymers containing sulfonic acid groups (e.g. a resin of the Amberlyst® brand from Rohm and Haas, such as Amberlyst®131). Further details are given below in context with methods A and B. Suitably, the water formed in the reaction is removed, generally by distillation, in order to promote the reaction. The reaction is generally carried out in an organic solvent, especially if an acid different from acidic cationic exchangers is used. Suitable solvents are e.g. alkanes, such as pentane or hexane, halogenated $C_1$-$C_4$-alkanes, such as dichloromethane, chloroform or dichloroethane, cycloalkanes, such as cyclohexane, aromatic hydrocarbons, such as toluene and the xylenes, aliphatic ethers, such as diethyl ether, diisopropylether or methyl-tert-buty ether, cyclic ethers, such as tetrahydrofuran or the dioxanes, or carboxylic acid esters, such as ethyl acetate. If an acidic cationic exchanger is used, the reaction can also be carried out neat, i.e. without solvent.

1 and 2 are usually applied in a molar ratio of 0.9:1 to 1.5:1 and preferably in a molar ratio of 1:1 to 1.3:1. It is expedient to use 1 in slight excess is order to avoid the formation of acetals as side products which would be favoured if 2 were used in excess.

Further details are given below in context with methods A and B.

The reaction generally results in a crude product mixture containing a compound of the formula (I) where $R^1$ is OH (termed I' in the following) one or more of compounds of formula (I) where one of $R^2$, $R^3$, $R^4$ together with $R^1$ represents a double bond (termed I" in the following). The dotted line is intended to show that one of the three dotted bonds is a double bond, whereas the other two are single bonds.

Scheme 1

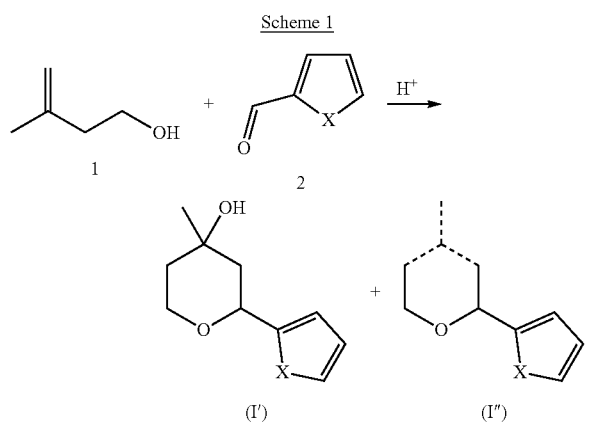

Compounds I' and I" can be separated from each other, if desired. If compound I" is a mixture of various double bond isomers, these can be separated from each other or enriched in one double bond isomer. Suitable separation and enrichment methods are known in the art and are for example distillative or chromatographic methods.

If desired, compounds I" can be hydrogenated to compounds I in which $R^1$ is H. Suitable hydrogenation conditions are described below in context with methods A and B.

If desired, compound I' can be dehydrated to give compounds I". Alternatively, if desired, compound I' can be alkylated to compounds I in which $R^1$ is O—$C_1$-$C_4$-alkyl, or acylated to compounds I in which $R^1$ is O—(C=O)—$R^5$. Suitable alkylation and acylation conditions are described below in context with methods A and B.

The invention also relates to a method for preparing compounds (I.a) and compounds (I.b). The reactions of the invention as described hereinafter are performed in reaction vessels customary for such reactions, the reaction being carried out in a continuous, semicontinuous or batchwise manner. In general, the particular reactions will be carried out under atmospheric pressure. The reactions may, however, also be carried out under reduced or elevated pressure.

To be more precise, the present invention relates to a method for preparing the compound of formula (I.a) or a mixture thereof, which method comprises the following step (i) and the optional steps (ii) to (iv):

(i) reacting 3-methylbut-3-en-1-ol with furan-2-carbaldehyde in the presence of a Brønsted acid to obtain a crude product mixture containing a compound of the formula (I) as defined herein, where X is O and $R^1$ is OH, and one or more of compounds of formula (I), where X is O and one of $R^2$, $R^3$, $R^4$ together with $R^1$ represents a double bond; and (ii) optionally isolating the compound of formula (I), where X is O and $R^1$ is OH; or, alternatively to step (ii), (iii) optionally separating the compounds of formula (I), where X is O and one of $R^2$, $R^3$, $R^4$ together with $R^1$ represents a double bond, from the compound of formula (I), where X is O and $R^1$ is OH, and subjecting the compounds of formula (I), where one of $R^2$, $R^3$, $R^4$ together with $R^1$ represents a double bond, to a hydrogenation reaction;

or, alternatively to steps (ii) and (iii), (iv) optionally subjecting the crude product mixture obtained in step (i) to a hydrogenation reaction and optionally isolating the compound of formula (I), where X is O and $R^1$ is H.

This method is in the following also referred to as method A.

Step (ii) leads to compounds (I.a) in which $R^1$ is OH, whereas steps (iii) and (iv) yield compounds (I.a) in which $R^1$ is H. Thus, in the first instance, method A yields compounds (I.a) in which $R^1$ is H or OH. The compound (I.a) obtained in step (ii) can however be further converted into compounds (I.a) in which $R^1$ is O—$C_1$-$C_4$-alkyl or O—(C=O)—$R^5$.

Accordingly, method A comprises an optional step (v):

(v) optionally subjecting the product obtained in step (ii) (i.e. the compound of formula (I.a), where $R^1$ is OH) or the reaction mixture as obtained in step (i) to an alkylation or acylation reaction (to yield compounds (I.a) in which $R^1$ is O—$C_1$-$C_4$-alkyl or O—(C=O)—$R^5$).

Generally, one of steps (ii), (iii) or (iv) has to be carried out; an exception being for example if the compound (I.a) obtained in step (ii) is to be further converted into a compound (I.a) in which $R^1$ is O—$C_1$-$C_4$-alkyl or O—(C=O)—$R^5$. In this case, the reaction mixture as obtained in step (i) can be used for the further conversion without preliminarily isolating in step (ii) the compound (I.a) in which $R^1$ is OH, although it is generally expedient to first isolate the compound (I.a) in which $R^1$ is OH in order to reduce the probability of the formation of undesired side products.

In the reaction in step (i) of the method A a crude product mixture containing a compound of formula (I), where X is O and $R^1$ is OH, i.e. a compound of formula (I.a), where $R^1$ is OH, and one or more of compounds of formula (I), where X is O one of $R^2$, $R^3$, $R^4$ together with $R^1$ represents a double bond, i.e. one or more of compounds of formulae (I-1), (I-2) or (I-3) as defined herein, where X in each case is O, is prepared. The conversion is effected by reacting isoprenol (3-methylbut-3-en-1-ol) 1 and furfural (furan-2-carbaldehyde) 2 as depicted in the reaction scheme 2 below (compare for example: U.S. Pat. No. 4,962,090, EP 0383446 and L. Liu et al., J. Am. Chem. Soc. 2016, 138, 10822-10825):

Scheme 2

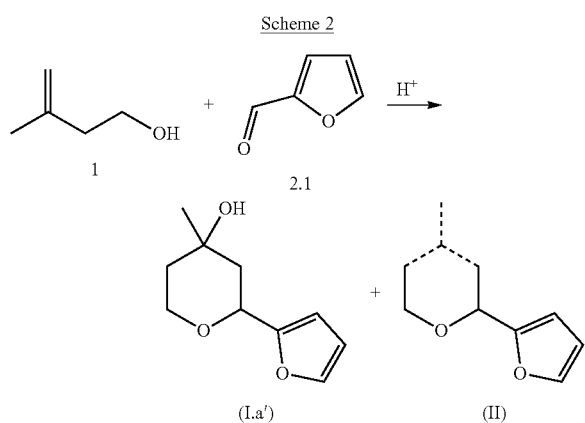

In scheme 2 the formula (II) represents one of the elimination products of formulae (I-1), (I-2) or (I-3) as defined herein, wherein X in each case is O, or any mixture of these elimination products. The formula (I.a') represents a compound of formula (I.a) where $R^1$ is OH.

In step (i) isoprenol and furfural undergo an addition reaction in the presence of a Brønsted acid as catalyst to yield a mixture of the tetrahydropyranol compound of the formula (I.a), where $R^1$ is OH, and one or more of the corresponding elimination products of the formula (II). This reaction may be regarded to belong to the group of reactions known in the art as Prins reactions.

Isoprenol and furfural are usually applied in a molar ratio of 0.9:1 to 1.5:1 and preferably in a molar ratio of 1:1 to 1.3:1. It is expedient to use isoprenol in slight excess is order to avoid the formation of acetals as side products which would be favoured if furfural were used in excess.

The Brønsted acid used in the reaction may be any Brønsted acid known in the art and is preferably selected from strong Brønsted acids, such as strongly acidic cation exchange resins, sulfuric acid, methanesulfonic acid and p-toluenesulfonic acid, specifically from methane sulfonic acid and strongly acidic cation exchange resins.

The term "strongly acidic cationic exchanger" refers to a cationic exchanger in the $H^+$ form which has strongly acidic groups. The strongly acidic groups are generally sulfonic acid groups; they are generally bonded to a polymer matrix, which can be e.g. gel-like and/or macroporous. Preference is given to styrene (co)polymers containing sulfonic acid groups, specifically to styrene-divinyl benzene copolymers containing sulfonic acid groups. Commercial examples for such cationic exchangers are Lewatit® (Lanxess), Purolite® (The Purolite Company), Dowex® (Dow Chemical Company), Amberlite® (Rohm and Haas Company), Amberlyst® (Rohm and Haas Company). Preferred strongly acidic cation exchangers are: Lewatit® K 1221, Lewatit® K 1461, Lewatit® K 2431, Lewatit® K 2620, Lewatit® K 2621, Lewatit® K 2629, Lewatit® K 2649, Amberlite® FPC 22, Amberlite® FPC 23, Amberlite® IR 120, Amberlyst® 131, Amberlyst® 15, Amberlyst® 31, Amberlyst® 35, Amberlyst® 36, Amberlyst® 39, Amberlyst® 46, Amberlyst® 70, Purolite® SGC650, Purolite® C100 H, Purolite® C150H, Dowex®50X8, Serdolit® red and Nafion® NR-50. Specifically, resins of the Amberlyst® brand from Rohm and Haas, and very specifically Amberlyst®131 is used. Alternatively, the cation exchanger can be a perfluorinated ion exchange resin, sold e.g. under the Nafion® brand of DuPont.

The Brønsted acid different from acidic cationic exchanger resins is generally used in catalytic amounts.

The amount of strongly acidic cation exchanger is not very critical, but yet for economic and processing aspects it is generally used in catalytic amounts. Usually, the strongly acidic cation exchanger is used in an amount of from about 5 up to about 40% by weight, preferably in an amount of from about 10 to about 40% by weight and particularly preferably in an amount of from about 15 to about 30% by weight, in each case based on the sum of the weights of 1 and 2. Here, the figures refer to the ready-to-use cation exchanger which is generally pretreated with water and accordingly can comprise amounts of up to about 70% by weight, preferably of about 30 to about 70% by weight and particularly preferably of about 40 to about 70% by weight of water. Particularly in the case of a discontinuous procedure, an additional addition of water when carrying out the process may therefore be superfluous. The specified strongly acidic cation exchangers can be used either individually or else in the form of mixtures.

If an acid different from acidic cationic exchangers is used in the reaction in step (i) of method A, the reaction is generally carried out in a suitable organic solvent that is inert under the reaction conditions of step (i). Suitable solvents are e.g. alkanes, such as pentane or hexane, halogenated $C_1$-$C_4$-alkanes, such as dichloromethane, chloroform or dichloroethane, cycloalkanes, such as cyclohexane, aromatic hydrocarbons, such as toluene and the xylenes, aliphatic ethers, such as diethyl ether, diisopropylether or methyl-tert-buty ether, cyclic ethers, such as tetrahydrofuran or the dioxanes, or carboxylic acid esters, such as ethyl acetate. The specified solvents can be used on their own or in the form of mixtures with one another. Specifically, an aromatic hydrocarbon is used. If an acidic cationic exchanger is used, the reaction can also be carried out in the presence of a solvent that is inert under the reaction conditions. Suitable solvents are those listed above. Generally however, when a strongly acidic cation exchanger is used as Brønsted acid, the reaction is carried out neat, i.e. without the addition of an organic solvent.

The reactants can in principle be contacted with one another in any desired sequence. For example, isoprenol and the Brønsted acid, optionally dissolved or dispersed in an inert solvent, can be initially charged and mixed with each other. The obtained mixture can then be admixed with furfural. Conversely, furfural, optionally dissolved or dispersed in an inert solvent, can be initially charged and admixed with a mixture of isoprenol and the Brønsted acid. Alternatively, furfural may first be mixed with the Brønsted acid and the mixture is then admixed with isoprenol. As a further alternative all reactants can be added simultaneously to the reaction vessel.

It has been found to be beneficial to initially charge the reaction vessel with a mixture of isoprenol and the Brønsted acid, possibly as a dispersion or solution in a solvent, but preferably without solvent, and then to add furfural, which is employed in dissolved form or, preferably, as such.

In general, the reaction in step (i) of method A is performed under temperature control. The reaction is typically effected in a closed or preferably in an open reaction vessel with stirring apparatus. The reaction temperature of reaction of method A depends on different factors, in particular on the acidity and the quantity used of the Brønsted acid, and can be determined by the person skilled in the art in the individual case, for example by simple preliminary tests. In general, the conversion of method A is performed at a temperature in the range from 10 to 150° C., preferably in the range from 30 to 120° C., more preferably in the range from 40 to 110° C. and specifically in the range from 50 to 100° C. In case that the obtention of dehydrated compounds II with C—C double bonds is desired, higher reaction temperatures, e.g. around 100° C., e.g. from 80 to 120° C. or 90 to 110° C., are expedient to promote the elimination and removal of water from intermediately formed compounds I.a'. If saturated compounds I.a' are desired, reaction temperatures below 100° C., such as 30 to 90° C. or 50 to 80° C. are more suitable.

The work-up of the reaction mixtures obtained in step (i) of method A and the isolation of the mixture of the compound of formula (I.a), where $R^1$ is OH, and one or more of the elimination products of the formula (II), are effected in a customary manner, for example by an aqueous extractive work-up or by removing the solvent, for example under reduced pressure. Generally, a mixture of the compound (I.a), where $R^1$ is OH, and one or more of the elimination products (II), is obtained in sufficient purity by applying such measures or a combination thereof. Thus, additional purification steps, in particular elaborated ones such as chromatography or distillation, are usually only required in case the separation of the elimination products of the formula (II) from the compound of formula (I.a), where $R^1$ is OH, is sought, as described herein below. However, if desired, further purification of a mixture of the compound (I.a), where $R^1$ is OH, and one or more of the elimination products (II) can be effected by methods commonly used in the art.

Preferably, the reaction mixture obtained in the step (i) of method A, for work-up, is diluted with a polar organic solvent that is insoluble or only slightly soluble in water and suitable for dissolving the reaction products obtained, such as e.g. ethyl acetate or dichloromethane. Afterwards the mixture is possibly filtered in order to remove the cation exchange resin that may have been used as Brønsted acid. The obtained product solution is then treated with an aqueous basic solution, such as aqueous sodium hydrogen carbonate. After removal of the aqueous phase, the organic phase is optionally treated again with the aforementioned aqueous basic solution. Preferably, the organic phase is afterwards washed with an aqueous solution having a neutral or approximately neutral pH value, such as brine. The organic phase containing the mixture of the compound (I.a), where $R^1$ is OH, and one or more of the elimination products (II) can then be introduced into a further reaction step, either directly or after partial or complete removal of the solvent. Alternatively, the organic phase is concentrated and the crude product thus obtained is subsequently retained for uses or sent directly to a use, for example used in a further reaction step, or subjected to further purification steps as described below.

In optional step (ii) of method A the compound (I.a), where $R^1$ is OH, is isolated from the mixture of the compound (I.a), where $R^1$ is OH, and the one or more elimination products (II) obtained in step (i). The isolation can be achieved by subjecting the mixture to at least one of the suitable purification procedures known in the art, such as distillation or chromatography, in particular distillation. In fact, the compound of formula (I.a) with $R^1$ being OH can be isolated from the mixture obtained in step (i) of method A by distillation in high purity.

In optional step (iii) of method A the mixture of the compound (I.a), where $R^1$ is OH, and the one or more elimination products (II) obtained in step (i) is subjected to a separation process in order to separate the one or more of the elimination products (II), i.e. the one or more of compounds of formula (I) with X being O and one of $R^2$, $R^3$, $R^4$ together with $R^1$ representing a double bond, from the compound (I.a), where $R^1$ is OH. The one or more of the elimination products (II) are then subjected to a hydrogenation reaction.

The separation can be achieved by employing one or more of the suitable purification procedures known in the art, such as distillation or chromatography, in particular distillation. In fact, the one or more of the elimination products (II) can be isolated from the mixture obtained in step (i) of method A by distillation in high purity.

In order to achieve a higher yield of the one or more elimination products (II) after the separation process it is typically beneficial to increase the proportion of the one or more elimination products (II) in the mixture of the compound (I.a), where $R^1$ is OH, and the one or more elimination products (II) obtained in step (i). This can be achieved by shifting the reaction equilibrium of the conversion in step (i) of method A in the direction of the elimination products of formula (II) by applying harsher reaction conditions, such as a higher reaction temperature, a greater amount of acid or a longer reaction time, or by removing water from the reaction equilibrium. If one or more of these measures are taken, the conversion of step (i) typically allows for the complete or nearly complete conversion of the starting materials isoprenol and furfural into the elimination products of the formula (II). Subsequent distillative purification according to step (iii) will then afford the one or more elimination products (II) in good yield and high purity.

The isolation of step (ii) and the separation of step (iii) can be typically conducted in a single purification run, such as in particular a single distillation run, to afford one fraction that consists, at least primarily, of compound of formula (I.a) with $R^1$ being OH and another fraction that consists, at least primarily, of the one or more of the elimination products (II).

In the hydrogenation reaction of step (iii) the one or more of the elimination products (II) obtained in the separation procedure are subjected to a hydrogenation reaction affording the tetrahydrofuran compound of the formula (I.a), where $R^1$ is H (termed I.a" in scheme 3), as shown in scheme 3 below.

Scheme 3

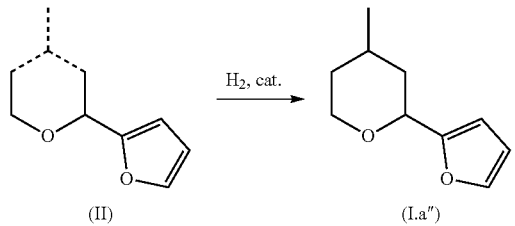

The hydrogenation can in principle be accomplished by using any hydrogenation method known in the art to be suitable for similar conversions. Preferably, the hydrogenation is conducted by employing gaseous hydrogen as reducing agent in the presence of a catalyst typically comprising at least one transition metal, in particular one from the groups IVB, VIIIB or IB of the Periodic Table (CAS version), for example zirconium, palladium, platinum, iron, cobalt, nickel, rhodium, iridium, ruthenium or copper. These metals may be present in the catalyst in the form of one of their salts, oxides or complexes, or, alternatively in metallic form. A preferred metal in this regard is nickel, especially in the form of Raney nickel. The hydrogenation in step (iii) can be carried out in analogy to the conversions described e.g. in J. H. Tyman et al., Tetrahedron Lett. 1970, 11, 4507; V. H. Rawal et al., J. Org. Chem. 1993, 58, 7718; B. M. Trost et al., J. Am. Chem. Soc. 2006, 128, 6745; L. Coulombel et al., Eur. J. Org. Chem. 2009, 33, 5788; and P. L. Alsters et al., Org. Process Res. Dev. 2010, 14, 259.

The hydrogenation in step (iii) of method A may be conducted without a solvent, but is preferably conducted in the presence of a solvent that is inert under the hydrogenation conditions, such as in particular a protic organic solvent preferably selected from $C_1$-$C_6$-alkanols, especially from methanol, ethanol and isopropanol.

The hydrogenation is typically carried at a hydrogen pressure in the range from 1 to 2 bar, preferably in the range from 1 to 1.5 bar and in particular from 1 to 1.2 bar. The temperature is usually in the range from 10 to 50° C. and preferably in the range from 20 to 40° C., e.g. from 20 to 30° C. or from 20 to 25° C.

The work-up of the reaction mixture obtained in step (iii) of method A and the isolation of the tetrahydrofuran compound of formula (I.a), where $R^1$ is H, are effected in a customary manner, for example by filtration and removal of the solvent, for example under reduced pressure. Generally, the product of formula (I.a) with $R^1$ being H is then obtained in sufficient purity and additional purification steps, such as chromatography or distillation are usually not necessary, but may be applied in case a very pure product of formula (I.a) with $R^1$ being H is desired.

In optional step (iv) of method A the mixture of the compound (I.a), where $R^1$ is OH, and one or more of the elimination products (II) obtained in step (i) is subjected to a hydrogenation reaction affording the tetrahydrofuran compound of formula (I.a) with $R^1$ being H, as shown in scheme 3 above.

The hydrogenation reaction in step (iv) is carried out in analogy to the one described herein above in the context of step (iii) of the method A.

In order to achieve a higher yield of the tetrahydrofuran compound of formula (I.a), where $R^1$ is H, in step (iv) of method A, it is typically beneficial to increase the proportion of the elimination products (II) in the mixture of the compound (I.a), where $R^1$ is OH, and one or more of the elimination products (II) obtained in step (i). This can be achieved by shifting the reaction equilibrium of the conversion in step (i) of method A in the direction of the elimination products of formula (II) by applying one or more of the measures described herein above.

Furthermore, the tetrahydropyranol compound of the formula (I.a), where $R^1$ is OH, obtained in step (i) or step (ii) of method A may be subjected to a alkylation reaction in order to prepare a compound of formula (I.a), where $R^1$ is O—$C_1$-$C_4$-alkyl.

The alkylation reaction is performed under conventional alkylation reaction conditions that are well known in the art. Preferably, the compound (I.a) with $R^1$ being O—$C_1$-$C_4$-alkyl is prepared by alkylating compound (I.a) with $R^1$ being OH using the alkylation reagent $R^6$—Y, wherein $R^6$ is a $C_1$-$C_4$-alkyl group and Y represents a leaving group, selected from halogen, such as Cl, Br, I, and sulfonates, such as tosylate, mesylate, triflate or nonaflate, typically in the presence of a base.

Suitable bases are typically selected from inorganic bases and organic bases.

Suitable inorganic bases that can be used in this alkylation reaction are for example alkali metal carbonates, e.g. $Li_2CO_3$, $Na_2CO_3$, $K_2CO_3$ or $Cs_2CO_3$, alkali metal hydroxides, e.g. LiOH, NaOH or KOH, and hydride donors, e.g. NaH, $LiAlH_4$ or $NaBH_4$.

Suitable organic bases that can be used in this alkylation reaction are for example tertiary amines, e.g. trimethylamine, triethylamine, tripropylamine, ethyldiisopropyl-amine and the like, or basic N-heterocycles, such as morpholine, pyridine, lutidine, DMAP, DABCO, DBU or DBN.

The work-up of the reaction mixtures obtained in the alkylation reaction and the isolation of the product of formula (I.a) with $R^1$ being O—$C_1$-$C_4$-alkyl are effected in a customary manner, for example by an aqueous extractive work-up or by removing the solvent, e.g. under reduced pressure. The desired product is generally obtained in sufficient purity by applying such measures or a combination thereof. However, additional purification steps, such as chromatography or distillation may be performed if a very pure compound of formula (I.a) with $R^1$ being O—$C_1$-$C_4$-alkyl is desired.

The tetrahydropyranol compound of the formula (I.a), where $R^1$ is OH, obtained in step (i) or step (ii) of method A may also be subjected to a acylation reaction in order to prepare a compound of formula (I.a), where $R^1$ is O—(C=O)—$R^5$.

Generally, the ester of formula (I.a) with $R^1$ being O—(C=O)—$R^5$ can efficiently be prepared by reacting the compound (I.a), where $R^1$ is OH, with the carboxylic acid $R^5$—COOH, wherein $R^5$ has one of the meanings defined herein, or an acid anhydride thereof, or a mixture of the carboxylic acid $R^5$—COOH with an acid anhydride thereof. The reaction is typically performed in the presence of an esterification catalyst or a base.

Suitable esterification catalysts that can be applied in this reaction are well known in the art. Suitable esterification catalysts are for example metal based catalysts, e.g. iron, cadmium, cobalt, lead, zinc, antimony, magnesium, titanium and tin catalysts in the form of metals, metal oxides or metal salts, such as metal alcoxylates, mineral acids, such as sulfuric acid, hydrochloric acid or phosphoric acid, or organic sulfonic acids, such as methane sulfonic acid or para-toluene sulfonic acid.

Suitable bases are for example organic bases, as defined above, such as in particular pyridine, lutidine or DMAP, specifically DMAP.

Alternatively, the ester of formula (I.a) with $R^1$ being O—(C=O)—$R^5$ can be prepared by reacting the compound (I.a), where $R^1$ is OH, with an acid halogenide of the formulae $R^5$—(C=O)Y', wherein $R^5$ has one of the meanings defined herein and Y' is halogen, such as Cl, Br or I, in the presence of an organic base, preferably one of those defined above.

Preferably, the ester of formula (I.a) with $R^1$ being O—(C=O)—$R^5$ is prepared by reacting the compound (I.a), where $R^1$ is OH, with an acid anhydride of the carboxylic acid $R^5$—COOH in the presence of an organic base.

The individual reaction conditions for the preparations of the ester of formula (I.a) with $R^1$ being O—(C=O)—$R^5$, as outlined above, are well known in the art.

The work-up of the reaction mixtures obtained in the acylation reaction and the isolation of the product of formula (I.a) with $R^1$ being O—(C=O)—$R^5$ are effected in a customary manner, for example by an aqueous extractive work-up or by removing the solvent, e.g. under reduced pressure. The desired product is generally obtained in sufficient purity by applying such measures or a combination thereof. However, additional purification steps, such as chromatography or distillation may be performed if a very pure compound of formula (I.a) with $R^1$ being O—(C=O)—$R^5$ is desired.

The present invention further relates to a method for preparing one of the compounds of formula (I.b) as defined herein above, or a mixture thereof, which method comprises the following step (i') and the optional steps (ii') to (v'):

(i') reacting 3-methylbut-3-en-1-ol with thiophene-2-carbaldehyde in the presence of a Brønsted acid to obtain a crude product mixture containing a compound of the formula (I.b), where $R^1$ is OH, and one or more of compounds of formula (I.b), where one of $R^2$, $R^3$, $R^4$ together with $R^1$ represents a double bond, (ii') optionally isolating the compound of formula (I.b), where $R^1$ is OH; or, alternatively to step (ii'), (iii') optionally separating the compounds of formula (I.b), where one of $R^2$, $R^3$, $R^4$ together with $R^1$ represents a double bond, from the compound of formula (I.b) where $R^1$ is OH, and, if desired, subjecting the compounds of formula (I.b), where one of $R^2$, $R^3$, $R^4$ together with $R^1$ represents a double bond, to a hydrogenation reaction;

or, alternatively to steps (ii') and (iii'), (iv') optionally subjecting the crude product mixture obtained in step (i) to a hydrogenation reaction and optionally isolating the compound of formula (I.b), where $R^1$ is H.

or, alternatively or additionally to steps (iii') and (iv'), (v') optionally subjecting the compound of formula (I.b), where $R^1$ is OH, to an alkylation or acylation reaction.

This method is herein also referred to as method B.

Step (ii') leads to compounds (I.b) in which $R^1$ is OH, step (iii') leads either to compounds (I.b) in which one of $R^2$, $R^3$, $R^4$ together with $R^1$ represents a double bond (if the hydrogenation reaction is not carried out), or, if the hydrogenation of such compounds is carried out, to compounds (I.b) in which $R^1$ is hydrogen, and step (iv') yields compounds (I.b) in which $R^1$ is H. Step (v') yields compounds (I.b) in which $R^1$ is O—$C_1$-$C_4$-alkyl or O—(C=O)—$R^5$.

Generally, one of steps (ii'), (iii') or (iv') has to be carried out; an exception being for example if the compound (I.b) obtained in step (ii) is to be further converted in step (v') into a compound (I.b) in which $R^1$ is O—$C_1$-$C_4$-alkyl or O—(C=O)—$R^5$. In this case, the reaction mixture as obtained in step (i) can be used in step (v') for the further conversion without preliminarily isolating the compound (I.b) in which $R^1$ is OH in step (ii'), although it is generally expedient to first isolate the compound (I.b) in which $R^1$ is OH in step (ii') in order to reduce the probability of the formation of undesired side products in step (v').

The steps (i') to (iv') of the method B correspond to the steps (i) to (iv) of method A of the present invention and can be carried out in analogy to the procedures described for the steps (i) to (iv) herein above, with the exception that in step (i') thiophene-2-carbaldehyde is used instead of furfural, and with the exception that in step (iii') the hydrogenation reaction can be skipped, so that compounds of formula (I.b), where one of $R^2$, $R^3$, $R^4$ together with $R^1$ represents a double bond, can be obtained. In addition, the alkylation and acylation reactions according to step (v') of method B correspond to the procedures described above for alkylating or acylating the tetrahydropyranol compound of the formula (I.a) with $R^1$ being OH and can be conducted in analogous fashion.

Compounds (I) different from compounds (I.a) and (I.b) (e.g. compounds (I) in which X is O and one of $R^2$, $R^3$, $R^4$ together with $R^1$ represents a double bond) can be prepared in an analogous manner. For example, compounds (I) in which X is O and one of $R^2$, $R^3$, $R^4$ together with $R^1$ represents a double bond can be prepared in analogy to method A, where however in step (iii) the hydrogenation step is skipped and the compounds (I) in which X is O and one of $R^2$, $R^3$, $R^4$ together with $R^1$ represents a double bond are isolated from the reaction mixture of step (i).

The following examples serve as further illustration of the invention.

EXAMPLES

1. Preparation Examples

Abbreviations

DMAP: 4-(dimethylamino)-pyridine
EA: ethyl acetate
RT: room temperature
THF: tetrahydrofuran
MTBE: methyl-tert-butyl ether
Analytics:

The purity of the products was determined by gas chromatography on the basis of area-%:

GC column: DB-WAX (30 m (length), 0.25 mm (ID), 0.25 micrometer (film);

Temperature program: 5 min at 50° C., 50° C. to 230° C. at 6° C./min, 10 min at 230° C.

Temperature of the injector 200° C.; temperature of the detector 230° C. Flow: 1.4 ml/min The products were identified by $^{13}$C NMR.

1a) Preparation of 2-(furan-2-yl)-4-methyl-tetrahydropyran-4-ol (Compound of Formula (I.a) with $R^1$=OH) and the Corresponding Three Elimination Products with an Exo- or Endocyclic Double Bond (Compounds of Formula (I) with X=O and $R^2$, $R^3$ or $R^4$ Together with $R^1$ Representing a Double Bond)

To a mixture of isoprenol (3-methylbut-3-en-1-ol) (40 g, 0.464 mol) and 20 g of the strongly acidic cation exchanger Amberlyst®131 (wet; from Rohm&Haas; washed with water, then with methanol and again with water before use) furfural (37.9 g, 0.395 mol) was slowly added at RT with stirring. The exothermic reaction was continued for 3 h at a temperature of 70° C. Afterwards the reaction mixture was set to RT and the cation exchanger was filtered off. The filtrate was mixed with 100 mL of EA and 100 mL of water. The organic phase was separated and washed with a saturated aqueous solution of $NaHCO_3$ and then with brine. The organic extracts were combined and dried with sodium sulfate. After evaporating the solvent at reduced pressure, 47.9 g of the crude product were obtained containing about 71.84% of 2-(furan-2-yl)-4-methyl-tetrahydropyran-4-ol and 19.95% of the elimination products 2-(furan-2-yl)-4-methylidene-tetrahydropyran, 2-(furan-2-yl)-4-methyl-5,6-dihydro-2H-pyran and 2-(furan-2-yl)-4-methyl-5,6-dihydro-2H-pyran, as per GC analysis (area %). The crude product was subjected to a distillative separation resulting in two main fractions. The first fraction of the distillation proved to be a mixture of the three elimination products with a purity of 95.3% (GC area %) and with a molar ratio of 1:65.5:33.5 of the of the compounds I-1:I-2:I-3, where in each case X is O.

Dihydropyran Analogs:

$^{13}$C NMR (125 MHz, $CDCl_3$): δ=22.97, 33.26, 65.79, 68.89, 106.77, 110.08, 119.64, 131.19, 142.21, 154.41.

Methylidene Analog:

¹³C NMR (125 MHz, CDCl₃): δ=34.82, 38.64, 68.47, 73.53, 106.78, 109.58, 110.06, 142.29, 143.28, 154.19.

The second fraction proved to be 2-(furan-2-yl)-4-methyl-tetrahydropyran-4-ol with a purity of 97.7% (GC area %) and a ratio of its E and Z isomers of 3:1, as determined by NMR.

E Isomer:

¹³C NMR (125 MHz, CDCl₃): δ=22.33, 26.11, 35.54, 39.81, 63.77, 68.28, 78.79, 106.74, 110.11, 142.29, 154.13, 170.32.

Z Isomer:

¹³C NMR (125 MHz, CDCl₃): δ=21.57, 22.41, 37.26, 40.66, 64.72, 69.93, 79.33, 106.70, 110.14, 142.31, 153.83, 170.24.

The reaction was repeated and 398.7 g of crude product were subjected to a fine distillation using a 60 cm column with a 4 cm diameter. 59 cm of the column were filled with column packing (DN30 A3-1000 2.4610 8 27×50 mm). Several fractions were isolated, fraction 4 being the isomer I-2 (with X=O) in a purity of 97.3%.

1b) Preparation of a Mixture of 2-(furan-2-yl)-dihydropyrans and 2-(furan-2-yl)-4-methylidene-tetrahydropyran with an Endo- or Exocyclic Double Bond (=Elimination Products of 2-(furan-2-yl)-4-methyl-tetrahydropyran-4-ol; Mixture of Compounds I-1, I-2 and I-3 with X=O=Mixture of Compounds of Formula (I) with X=O and R², R³ or R⁴ Together with R¹ Representing a Double Bond)

A mixture of isoprenol (21.50 g, 0.249 mol) and furfural (20 g, 0.208 mol) in 200 mL of toluene was stirred at 20° C. At this temperature, 2 drops of methansulfonic acid were added to the reaction mixture (light exotherm). The mixture was stirred at reflux for 5 h while water was being distilled during the reaction. Afterwards, the reaction mixture was set to RT. To the mixture 100 mL of water were added and the organic phase was washed with a 5% solution of NaHCO₃ and with water. The organic extracts were combined and dried with sodium sulfate. After evaporating the solvent at reduced pressure, 30.3 g of the crude product were obtained containing about 6% of 2-(furan-2-yl)-4-methyl-tetrahydropyran-4-ol and 80.7% of the elimination products 2-(furan-2-yl)-4-methylidene-tetrahydropyran, 2-(furan-2-yl)-4-methyl-5,6-dihydro-2H-pyran and 2-(furan-2-yl)-4-methyl-5,6-dihydro-2H-pyran, as per GC analysis (area %). The crude product was subjected to a distillative separation resulting in a major fraction that proved to be a mixture of the three elimination products with a purity of 97.8% (GC area %) and with a molar ratio of 1:19.5:79.5 of the compounds I-1:I-2:I-3, where in each case X is O.

The reaction was repeated and 59.9 g of crude product were subjected to a fine distillation using a 21 cm column filled with column packing (DN30 A3-1000 2.4610 8 27×50 mm). Several fractions were isolated, fraction 3 containing 7% of I-2 and 92% of I-3, where in each case X is O.

1c) Preparation of 2-(2-furan-2-yl)-4-methyl-tetrahydropyran (Compound of Formula (I.a) with R¹ Being H)

15 g of a mixture of the three elimination products I-1, I-2 and I-3 with X=O with an exo- or endocyclic double bond (compounds of formula (I) with X=O and R², R³ or R⁴ together with R¹ representing a double bond) were dissolved in 360 mL of methanol. To this mixture 9 g of Raney nickel (50% in water) was added. The reaction vessel was connected to a gasburet filled with water. Then H₂ was pressed directly from the gas-bottle into the gasburet in a way that the H₂ consumption could be monitored. The reaction proceeded at 25° C. The experiment was continued for 4.5 h and a 2.5 L consumption of H₂ was observed. The catalyst was filtered off and the solvent was evaporated at reduced pressure. 16.2 g of crude product were obtained that contained 95% of the hydrogenated product. The crude product was subjected to a distillative separation resulting in a major fraction that proved to be the desired 2-(2-furyl)-4-methyl-tetrahydropyran in a 3:2 Z/E ratio with a 96% purity.

Z Isomer:

¹³C NMR (125 MHz, CDCl₃): δ=22.25, 30.18, 34.25, 38.13, 68.27, 72.81, 106.02, 110.01, 141.83, 155.13.

E Isomer:

¹³C NMR (125 MHz, CDCl₃): δ=20.19, 25.22, 33.00, 35.26, 62.60, 68.27, 107.18, 109.99, 141.83, 154.84.

1d) Preparation of 2-(furan-2-yl)-4-methyl-tetrahydropyran-4-yl-acetate (Compound of Formula (I.a) with R¹ Being O—(C=O)—CH₃)

DMAP (0.2 g, 1.64 mmol) was added to a solution of 2-(furan-2-yl)-4-methyl-tetrahydropyran-4-ol (10 g, 0.055 mol) in 50 mL of THE at RT. The obtained mixture was refluxed at 53° C. while acetic anhydride (7 g, 1.25 eq.) was slowly added at this temperature. After 6 h, approximately 85% conversion was observed by GC. The reaction was cooled down to RT and slowly quenched with 50 mL of water. Afterwards 50 mL of EA were added. The organic phase was separated and washed with a saturated aqueous solution of NaHCO₃ and the with brine. The organic extracts were combined and dried with sodium sulfate. After evaporating the solvent at reduced pressure 6.9 g of a crude product was obtained containing about 81.5% of the title compound, as per GC analysis (area %). Purification by column chromatography afforded the title compound having a purity of 99% (GC area %) as a mixture of its E and Z isomers. NMR analysis revealed a E/Z isomer ratio of 7:3.

E Isomer:

¹³C NMR (125 MHz, CDCl₃): δ=31.59, 38.14, 42.03, 63.94, 67.52, 68.44, 106.65, 110.03, 142.16, 154.61.

Z Isomer:

¹³C NMR (125 MHz, CDCl₃): δ=25.19, 40.05, 43.58, 65.59, 68.55, 70.66, 106.75, 110.13, 142.25, 154.05.

1e) Preparation of 2-(2-furan-2-yl)-4-methoxy-4-methyl-tetrahydropyran (Compound of Formula (I.a) with R¹ Being OCH₃)

To a dispersion of sodium hydride (1.3 eq) in 75 mL of THE a solution of 10 g of 2-(furan-2-yl)-4-methyl-tetrahydropyran-4-ol (compound of formula (I.a) with R¹=OH) in 30 mL of THE was slowly added at 0° C. The mixture was stirred for 30 min at 0° C. Then 1.3 eq of methyl iodide were slowly added at RT. After the addition, the mixture was stirred at 40° C. for 4 h. The reaction mixture was cooled to 0° C. and the addition of 0.25 eq of NaH followed by 0.25 eq of methyl iodide was repeated. The mixture was then stirred for 17 h at 40° C. The reaction was slowly quenched with 50 mL of water. The organic phase was extracted with 3 times 50 mL of MTBE. The organic extracts were combined and washed with 50 mL of NH₃ solution and with 50 mL of brine. The organic extracts were combined and dried with sodium sulfate. After evaporating the solvent at reduced pressure 9.6 g of crude product were obtained containing 95% of the desired methyl ether according to the GC (area %). The crude product was subjected to a distillative separation resulting in a major fraction that proved to be the desired 2-(2-furan-2-yl)-4-methoxy-4-methyl-tetrahydropyran with a purity of 99% (GC area %). NMR analysis indicated a E/Z mixture in a ratio 7:3.

E Isomer:
$^{13}$C NMR (125 MHz, CDCl$_3$): δ=24.84, 34.92, 39.22, 48.69, 63.77, 68.12, 71.18, 106.44, 110.01, 142.13, 154.84.

Z Isomer:
$^{13}$C NMR (125 MHz, CDCl$_3$): δ=20.26, 36.59, 40.33, 48.20, 65.43, 70.42, 72.48, 106.51, 110.11, 142.20, 154.35.

1f) Preparation of 2-(thien-2-yl)-4-methyl-tetrahydropyran-4-ol (Compound of Formula (I.b) with R$^1$ Being OH and R$^2$, R$^3$ and R$^4$ Being Each H)

To a mixture of isoprenol (20 g, 0.232 mol) and 10 g of the strongly acidic cation exchanger Amberlyst® 131 (wet; from Rohm&Haas) thiopene-2-carbaldehyde (22.13 g, 0.197 mol) was slowly added at RT with stirring. The exothermic reaction was continued for 3 h at a temperature of 70° C. Afterwards the reaction mixture was set to RT and the cation exchanger was filtered off. The filtrate was mixed with 100 mL of EA and 100 mL of water. The organic phase was separated and washed with a saturated aqueous solution of NaHCO$_3$ and then with brine. The organic extracts were combined and dried with sodium sulfate. After evaporating the solvent at reduced pressure, 28.5 g of the crude product were obtained containing about 67.45% of 2-(thien-2-yl)-4-methyl-tetrahydropyran-4-ol and 14.68% of the elimination products 2-(thien-2-yl)-4-methylidene-tetrahydropyran, 2-(thien-2-yl)-4-methyl-5,6-dihydro-2H-pyran and 2-(thien-2-yl)-4-methyl-5,6-dihydro-2H-pyran, as per GC analysis (area %). The crude product was subjected to a distillative separation resulting in two main fractions. The major fraction was 2-(thien-2-yl)-4-methyl-tetrahydropyran-4-ol with a purity of 98.2% (GC area %) and a ratio of its E and Z isomers of 55:45, as determined by NMR.

E Isomer:
$^{13}$C NMR (125 MHz, CDCl$_3$): δ=31.55, 38.14, 46.23, 64.14, 67.86, 71.07, 123.57, 124.47, 126.38, 145.80.

Z Isomer:
$^{13}$C NMR (125 MHz, CDCl$_3$): δ=25.19, 40.01, 47.73, 65.79, 68.76, 73.22, 123.74, 124.78, 126.38, 145.09.

1g) Preparation of a Mixture of 2-(thiophen-2-yl)-dihydropyrans and 2-(thiophen-2-yl)-4-methylidene-tetrahydropyran with an Endo- or Exocyclic Double Bond (=Elimination Products of 2-(thiophen-2-yl)-4-methyl-tetrahydropyran-4-ol; Mixture of Compounds I-1, I-2 and I-3 with X=S=Mixture of Compounds of Formula (Ib) in which R$^2$, R$^3$ or R$^4$ Together with R$^1$ Represent a Double Bond)

To a solution of the distillated product from example 1f) (5.5 g, 0.027 mol) in 35 mL of toluene were slowly added 0.8 g of NaHSO$_4$ (0.007 mol) at RT. The reaction was stirred at 110° C. (reflux) for 3 h. After this time, 37% conversion of the 2-(thien-2-yl)-4-methyl-tetrahydropyran-4-ol was observed and the reaction was stopped. The mixture was cooled to RT and NaHSO$_4$ was filtered off. To the filtrate 50 mL of water were added. The organic phase was separated and washed with water and brine. The organic extracts were combined and dried with sodium sulfate. After evaporating the solvent at reduced pressure, 2.4 g of crude product were obtained containing about 61% of 2-(thien-2-yl)-4-methyl-tetrahydropyran-4-ol and 36% of the elimination products 2-(thien-2-yl)-4-methylidene-tetrahydropyran, 2-(thien-2-yl)-4-methyl-5,6-dihydro-2H-pyran and 2-(thien-2-yl)-4-methyl-5,6-dihydro-2H-pyran, as per GC analysis (area %). Purification by column chromatography afforded the title compounds with a purity of 98.8% (GC area %) and with a molar ratio of 1:39:60 of the compounds I-1:I-2:I-3, where in each case X is S.

Dihydropyran Analogs:
$^{13}$C NMR (125 MHz, CDCl$_3$): δ=22.91, 37.33, 66.15, 71.55, 119.72, 123.77, 124.68, 126.43, 131.37, 145.59.

Methylidene Analog:
$^{13}$C NMR (125 MHz, CDCl$_3$): δ=34.77, 42.78, 68.89, 76.37, 109.46, 123.64, 124.69, 126.45, 143.53, 145.37.

1h) Preparation of 2-(2-furan-2-yl)-4-ethoxy-4-methyl-tetrahydropyran (Compound of Formula (I.a) with R$^1$ being OCH$_2$CH$_3$)

To a dispersion of sodium hydride (1.3 eq) in 70 mL of toluene a solution of 12 g of 2-(furan-2-yl)-4-methyl-tetrahydropyran-4-ol (compound of formula (I.a) with R$^1$=OH) in 20 mL of toluene was slowly added at 0° C. The mixture was stirred for 30 min at 0° C. The reaction was heated to 87° C. for 2 h and at this temperature 0.7 eq of diethylsulfate were slowly added. After the addition, the mixture was stirred at 87° C. for 3 h. The reaction was slowly quenched with 50 mL of water and the mixture was then stirred for 48 h at RT. The organic phase was separated and dried with sodium sulfate. After evaporating the solvent at reduced pressure 11.2 g of crude product were obtained containing 90% of the desired ethyl ether according to the GC (area %) in a Z/E ratio of 30:60. Purification by column chromatography resulted in two major fractions that proved to be the desired 2-(2-furan-2-yl)-4-ethoxy-4-methyl-tetrahydropyran. NMR analysis indicated that the first fraction was the E isomer (95% purity [GC area %]) and the second fraction was a Z/E mixture in a ratio 85:15 (97% purity [GC area %]).

E Isomer:
$^{13}$C NMR (125 MHz, CDCl$_3$): δ=16.01, 25.57, 35.45, 39.66, 56.06, 63.87, 68.18, 71.00, 106.39, 110.01, 142.10, 154.96.

Z Isomer:
$^{13}$C NMR (125 MHz, CDCl$_3$): δ=16.13, 20.99, 37.10, 40.85, 55.52, 65.42, 70.38, 72.29, 106.48, 110.10, 142.17, 155.46.

2. Olfactory Tests

In order to test the quality and intensity of the odor of the compounds (I) of the present invention, scent strip tests were performed.

For this purpose, strips of absorbent paper were dipped into solution containing 1 to 10% by weight solution of the compound (I) to be tested in ethanol. After evaporation of the solvent (about 30 sec.) the scent impression was olfactively evaluated by a trained perfumer.

The results of the scent test are summarized in table 1.

TABLE 1

Results of the scent tests.

| Example no. | Compound | Odor Description |
|---|---|---|
| 1.1 | 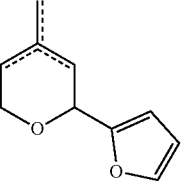<br>1st fraction of example 1a)<br>Isomers of formulae (I-1), (I-2) and (I-3), where in each case X = O, at a molar ratio of 1:65.5:33.5 | Galbanum, Herbal, Smoky, Leather |
| 1.2 | 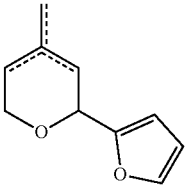<br>Product of fine distillation of 1b)<br>Isomers of formulae (I-2) and (I-3), where in each case X = O, at a molar ratio of 7:92 | Spicy, Nutmeg, Smoky, Tobacco, Leather, Phenol |
| 1.3 | 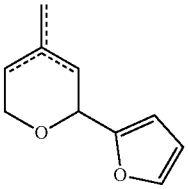<br>Product of fine distillation of 1a)<br>Isomer of formula (I-2), where X = O, with a purity o 97.3% | Root, Galbanum, Leather, Spicy |
| 1.4 | 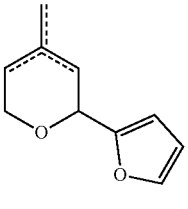<br>Compound of example 1b)<br>Isomers of formulae (I-1), (I-2) and (I-3), where in each case X = O, at a molar ratio of 1:19.5:79.5 | Herbal, Smoky, Spicy, Nutmeg, Galbanum, Leather, Oakmoss |
| 1.5 | 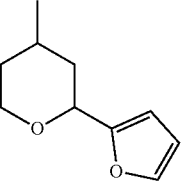<br>Compound of example 1c)<br>Compound of formula (I.a), where $R^1$ = H, with E/Z ratio of 2:3 | Smoked, Lime, Hickory, Green, Sweet |
| 1.6 | 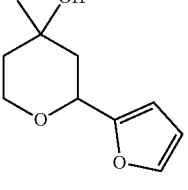<br>2nd fraction of example 1a)<br>Compound of formula (I.a), where $R^1$ = OH, with E/Z ratio of 3:1 | Galbanum, Floral |
| 1.7 | 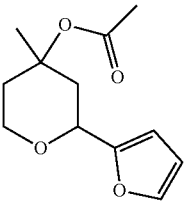 [SMILES: CC(=O)OC1(C)CCOC(c2ccco2)C1]<br>Compound of example 1d)<br>Compound of formula (I.a), where $R^1$ = O—(C=O)—CH$_3$, with E/Z ratio of 7:3 | Weak |
| 1.8 | <br>Compound of example 1e)<br>Compound of formula (I.a), where $R^1$ = O—CH$_3$, with E/Z ratio of 7:3 | Watery, melon, slightly bitter |
| 1.9 | <br>Product of example 1g)<br>Isomers of formulae (I-1), (I-2) and (I-3), where in each case X = S, at a molar ratio of 1:39:60 | Green, Herbal, Chives, Woody |
| 1.10 | <br>Compound of example 1f)<br>Compound of formula (I.b), where $R^1$ = OH, with E/Z ratio of 55:45 | Beer, Burnt |

The invention claimed is:
1. A composition comprising an aroma chemical, wherein the aroma chemical is a compound of the general formula (I)

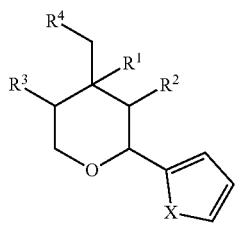

(I)

wherein

X is O or S;

R$^1$ is hydrogen, OH, O—C$_1$-C$_4$-alkyl or O—(C=O)—R$^5$;

R$^2$, R$^3$, R$^4$ are hydrogen;

or one of R$^2$, R$^3$, R$^4$ together with R$^1$ represents a double bond; and

R$^5$ is selected from the group consisting of hydrogen and C$_1$-C$_4$-alkyl;

a mixture of two or more different compounds of the general formula (I), a stereoisomer thereof or a mixture of stereoisomers thereof.

2. The composition according to claim 1, where the compound of the formula (I) is a compound I-1, I-2 or I-3, where the compound I-1 is a compound of the formula (I) in which R$^2$ together with R$^1$ represents a double bond, the compound I-2 is a compound of the formula (I) in which R$^3$ together with R$^1$ represents a double bond and the compound I-3 is a compound of the formula (I) in which R$^4$ together with R$^1$ represents a double bond; or is a mixture of at least two compounds I-1, I-2 and I-3.

3. The composition according to claim 2, where the mixture contains compounds I-2 and I-3 and optionally also compound I-1, where compound I-1 is contained in an amount of from 0 to 10% by weight, compound I-2 is contained in an amount of from 1 to 80% by weight, and compound I-3 is contained in an amount of from 15 to 99% by weight, relative to the total weight of compounds I-1, I-2 and I-3.

4. The composition according to claim 1, where in formula (I) R$^1$ is hydrogen.

5. The composition according to claim 1, where in formula (I) R$^1$ is OH.

6. The composition according to claim 1, where in formula (I) R$^1$ is O—C$_1$-C$_4$-alkyl.

7. The composition according to claim 1, where in formula (I) R$^1$ is O—(C=O)—R$^5$.

8. The composition according to claim 1, where X is O.

9. The composition according claim 1, where X is S.

10. The composition according to claim 1, wherein the composition imparts an olfactory impression.

11. The composition according to claim 10, wherein the composition is a fragrance.

12. A fragranced ready-to-use composition comprising a compound of general formula (I) as defined in claim 1, a stereoisomer thereof, a mixture of stereoisomers thereof or a mixture of different compounds of the general formula (I) as defined in claim 1, for modifying the scent character of the fragranced ready-to-use composition.

13. The composition according to claim 1, wherein the composition is selected from perfume compositions, body care compositions, products for oral and dental hygiene, hygiene articles, cleaning compositions, textile detergent compositions, compositions for scent dispensers, foods, food supplements, pharmaceutical compositions and crop protection compositions.

14. A composition comprising at least one compound of the general formula (I) as defined in claim 1, a mixture thereof, a stereoisomer thereof or a mixture of stereoisomers of at least one compound of the general formula (I) as defined in claim 1, and at least one further compound selected from the group consisting of aroma chemicals different from compounds of the general formula (I) and non-aroma chemical carriers.

15. The composition according to claim 14, where the non-aroma chemical carriers are selected from the group consisting of surfactants, emollients and solvents, where the solvents are selected from the group consisting of ethanol, isopropanol, propylene glycol, dipropylene glycol, 1,2-butylene glycol, diethylene glycol monoethyl ether, glycerol, diethyl phthalate, isopropyl myristate, triethyl citrate, and benzyl benzoate.

16. The composition according to claim 14, which is selected from the group consisting of perfume compositions, body care compositions, products for oral and dental hygiene, hygiene articles, cleaning compositions, textile detergent compositions, compositions for scent dispensers, foods, food supplements, pharmaceutical compositions and crop protection compositions.

17. A compound of the general formula (I.a)

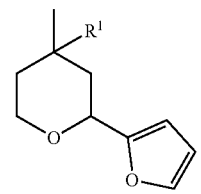

(I.a)

wherein

R$^1$ is hydrogen, OH, O—C$_1$-C$_4$-alkyl or O—(C=O)—R$^5$,

R$^5$ is selected from the group consisting of hydrogen and C$_1$-C$_4$-alkyl;

a mixture thereof, a stereoisomer thereof or a mixture of stereoisomers thereof.

18. The compound according to claim 17, wherein R$^1$ is OH, O—C$_1$-C$_4$-alkyl or O—(C=O)—R$^5$.

19. A compound of the general formula (I.b)

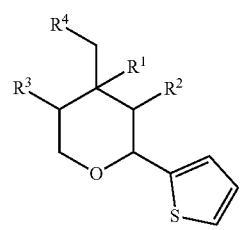

(I.b)

wherein

R$^1$ is hydrogen, OH, O—C$_1$-C$_4$-alkyl or O—(C=O)—R$^5$,

R$^2$, R$^3$, R$^4$ are hydrogen;

or one of R$^2$, R$^3$, R$^4$ together with R$^1$ represents a double bond;

$R^5$ is selected from the group consisting of hydrogen and $C_1$-$C_4$-alkyl;

a mixture thereof, a stereoisomer thereof or a mixture of stereoisomers thereof.

20. A mixture of at least two different compounds of formula (I) as defined in claim 1; where the mixture is a mixture of a least two compounds I-1, I-2 and I-3, where in compound I-1 $R^2$ together with $R^1$ represents a double bond, in compound I-2 $R^3$ together with $R^1$ represents a double bond, and in compound I-3 $R^4$ together with $R^1$ represents a double bond.

21. The mixture according to claim 20, where X is S.

22. The mixture according to claim 20, where the mixture contains compounds I-2 and I-3 and optionally also compound I-1, where compound I-1 is contained in an amount of from 0 to 10% by weight, compound I-2 is contained in an amount of from 1 to 80% by weight, and compound I-3 is contained in an amount of from 15 to 99% by weight, relative to the total weight of compounds I-1, I-2 and I-3.

23. A method for preparing the compound of formula (I.a) according to claim 17, or a mixture of different compounds (I.a), which method comprises: for preparing the compound of formula (I.a) where $R^1$ is OH or H or a mixture thereof:

(i) reacting 3-methylbut-3-en-1-ol with furan-2-carbaldehyde in the presence of a Brønsted acid to obtain a crude product mixture containing a compound of the formula (I) as defined in claim 1, where X is O and $R^1$ is OH, and one or more of compounds of formula (I), where X is O and one of $R^2$, $R^3$, $R^4$ together with $R^1$ represents a double bond; and (ii) optionally isolating the compound of formula (I), where X is O and $R^1$ is OH; or, alternatively to step (ii), (iii) optionally separating the compounds of formula (I), where X is O and one of $R^2$, $R^3$, $R^4$ together with $R^1$ represents a double bond, from the compound of formula (I), where X is O and $R^1$ is OH, and subjecting the compounds of formula (I), where one of $R^2$, $R^3$, $R^4$ together with $R^1$ represents a double bond, to a hydrogenation reaction; or, alternatively to steps (ii) and (iii), (iv) optionally subjecting the crude product mixture obtained in step (i) to a hydrogenation reaction and optionally isolating the compound of formula (I), where X is O and $R^1$ is H;

and for preparing the compound of formula (I.a), where $R^1$ is O—$C_1$-$C_4$-alkyl or O—(C=O)—$R^5$:

(v) subjecting the compound of formula (I.a), where $R^1$ is OH, to an alkylation or acylation reaction.

24. A method for preparing the compound of formula (I.b) according to claim 19, or a mixture of different compounds of formula (I.b), which method comprises (i') reacting 3-methylbut-3-en-1-ol with thiophene-2-carbaldehyde in the presence of a Brønsted acid to obtain a crude product mixture containing a compound of the formula (I.b) where $R^1$ is OH, and one or more of compounds of formula (I.b) where one of $R^2$, $R^3$, $R^4$ together with $R^1$ represents a double bond, (ii') optionally isolating the compound of formula (I.b), where $R^1$ is OH; or, alternatively to step (ii'), (iii') optionally separating the compounds of formula (I.b), where one of $R^2$, $R^3$, $R^4$ together with $R^1$ represents a double bond, from the compound of formula (I.b) where $R^1$ is OH and, if desired, subjecting the compounds of formula (I.b), where one of $R^2$, $R^3$, $R^4$ together with $R^1$ represents a double bond, to a hydrogenation reaction; or, alternatively to steps (ii') and (iii'), (iv') optionally subjecting the crude product mixture obtained in step (i) to a hydrogenation reaction and optionally isolating the compound of formula (I.b), where $R^1$ is H; or, alternatively to steps (iii') and (iv'), (v') optionally subjecting the compound of formula (I.b), where $R^1$ is OH, to an alkylation or acylation reaction.

25. A mixture of at least two different compounds of formula (I)

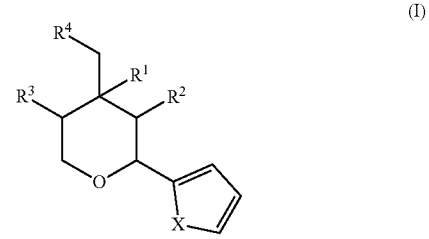

(I)

wherein
X is S;
$R^1$ is hydrogen, OH, O—$C_1$-$C_4$-alkyl or O—(C=O)—$R^5$;
$R^2$, $R^3$, $R^4$ are hydrogen;
or one of $R^2$, $R^3$, $R^4$ together with $R^1$ represents a double bond; and
$R^5$ is selected from the group consisting of hydrogen and $C_1$-$C_4$-alkyl.

\* \* \* \* \*